US012636123B2

(12) United States Patent
Nguyen et al.

(10) Patent No.: US 12,636,123 B2
(45) Date of Patent: May 26, 2026

(54) DENTAL MOUTHPIECE

(71) Applicant: SOLMETEX, LLC, Northborough, MA (US)

(72) Inventors: Thien Nguyen, Santa Ana, CA (US); Tam Thanh Pham, San Francisco, CA (US); Ethan Nguyen, Santa Ana, CA (US); Lauren Nguyen, Santa Ana, CA (US)

(73) Assignee: Solmetex, LLC, Northborough, MA (US)

( * ) Notice: Subject to any disclaimer, the term of this patent is extended or adjusted under 35 U.S.C. 154(b) by 34 days.

(21) Appl. No.: 18/983,258

(22) Filed: Dec. 16, 2024

(65) Prior Publication Data

US 2025/0177092 A1 Jun. 5, 2025

Related U.S. Application Data

(63) Continuation of application No. 18/376,309, filed on Oct. 3, 2023, now Pat. No. 12,167,948, which is a
(Continued)

(51) Int. Cl.
 *A61C 5/90* (2017.01)
 *A61B 1/24* (2006.01)
(Continued)

(52) U.S. Cl.
 CPC .................. *A61C 5/90* (2017.02); *A61B 1/24* (2013.01); *A61C 7/08* (2013.01); *A61C 17/08* (2019.05)

(58) Field of Classification Search
 CPC ........... A61C 5/90; A61C 17/08; A61C 17/06; A61C 17/10; A61C 17/0211; A61C 17/04;
(Continued)

(56) References Cited

U.S. PATENT DOCUMENTS

| | | | |
|---|---|---|---|
| 50,461 | A | 10/1865 | Dibble |
| 1,471,207 | A | 10/1923 | Napoleon |

(Continued)

FOREIGN PATENT DOCUMENTS

| | | |
|---|---|---|
| AU | 2020274979 | 12/2025 |
| BR | 112021022474 A2 | 1/2022 |

(Continued)

OTHER PUBLICATIONS

Nguyen; Thien, Intraoral Device, Claims received on Feb. 12, 2025, U.S. Pat. No. 20240423768 AI (Year: 2024).
(Continued)

*Primary Examiner* — Edelmira Bosques
*Assistant Examiner* — Holly T. To
(74) *Attorney, Agent, or Firm* — Polsinelli LLP

(57) ABSTRACT

A dental mouthpiece is provided that may be attached to a high-suction dental adapter for the purpose of assisting the dental staff during dental procedures through chair-side, hands-free suction, and isolation. Such a mouthpiece may comprise a main body portion, a cheek retractor portion, and a suction connector portion. In an embodiment, the main body portion, cheek retractor portion, and suction connector portion may be molded in one piece, preferably by injection molding. The main body portion has an anterior wall inside the curve and a posterior wall outside the curve, and an at least one connector connecting the anterior wall and the posterior wall. The main body portion has an anterior intervening wall and the posterior intervening wall in between the anterior and posterior walls. The anterior intervening wall and the posterior intervening walls have alternating crests and troughs.

30 Claims, 10 Drawing Sheets

Related U.S. Application Data continuation of application No. 16/870,745, filed on May 8, 2020, now Pat. No. 11,826,217.

(60) Provisional application No. 62/846,353, filed on May 10, 2019.

(51) Int. Cl.
*A61C 7/08* (2006.01)
*A61C 17/08* (2006.01)

(58) Field of Classification Search
CPC .............. A61C 17/043; A61C 17/0208; A61B 2017/222079; A61B 2218/001; A61B 2218/007; A61B 2090/401; A61B 1/24; A61F 5/566
See application file for complete search history.

(56) References Cited

U.S. PATENT DOCUMENTS

| | | | |
|---|---|---|---|
| 1,731,322 A | 10/1929 | Riddle | |
| 2,019,612 A | 11/1935 | Langhans et al. | |
| 2,937,445 A | 5/1960 | Erickson | |
| 3,090,122 A | 5/1963 | Erickson | |
| 3,101,543 A | 8/1963 | Baughan | |
| 3,247,844 A | 4/1966 | Berghash | |
| 3,379,192 A | 4/1968 | Warren | |
| 3,453,735 A | 7/1969 | Burt | |
| 3,489,141 A | 1/1970 | Warren | |
| 3,516,160 A | 6/1970 | Leffler | |
| 3,758,950 A | 9/1973 | Krouzian | |
| 3,768,477 A | 10/1973 | Anders et al. | |
| 3,802,081 A | 4/1974 | Rogers | |
| 3,857,181 A | 12/1974 | Rappaport | |
| 3,877,691 A | 4/1975 | Foster | |
| 3,924,333 A | 12/1975 | Erickson | |
| 4,017,975 A | 4/1977 | Johnson | |
| 4,024,642 A | 5/1977 | Zorovich | |
| 4,083,115 A | 4/1978 | McKelvey | |
| 4,167,814 A | 9/1979 | Schubert | |
| 4,192,071 A | 3/1980 | Erickson | |
| 4,237,574 A | 12/1980 | Kelly et al. | |
| D267,586 S | 1/1983 | Hatlen | |
| 4,425,911 A | 1/1984 | Luomanen | |
| 4,511,329 A | 4/1985 | Diamond | |
| 4,718,662 A | 1/1988 | North | |
| 4,802,851 A | 2/1989 | Rhoades | |
| 4,822,278 A | 4/1989 | Oliva et al. | |
| 4,975,057 A | 12/1990 | Dyfvermark | |
| D315,955 S | 4/1991 | Mann | |
| 5,009,595 A | 4/1991 | Osborn | |
| 5,037,298 A | 8/1991 | Hickham | |
| 5,078,602 A | 1/1992 | Honoshofsky | |
| 5,365,624 A | 11/1994 | Berns | |
| 5,460,524 A | 10/1995 | Anderson | |
| D364,456 S | 11/1995 | Solnit | |
| 5,516,286 A | 5/1996 | Kushner | |
| D372,096 S | 7/1996 | Frush | |
| 5,588,836 A | 12/1996 | Landis et al. | |
| 5,720,275 A | 2/1998 | Patil et al. | |
| 5,730,599 A | 3/1998 | Pak | |
| 5,762,496 A | 6/1998 | Albertsson et al. | |
| 5,890,899 A | 4/1999 | Sclafani | |
| 6,022,214 A | 2/2000 | Hirsch et al. | |
| 6,213,772 B1 | 4/2001 | Costello | |
| 6,223,376 B1 | 5/2001 | Lee | |
| 6,241,521 B1 | 6/2001 | Garrison | |
| 6,267,591 B1 | 7/2001 | Barstow | |
| 6,338,627 B2 | 1/2002 | Hirsch et al. | |
| 6,575,746 B2 | 6/2003 | Hirsch et al. | |
| 6,652,276 B2 | 11/2003 | Fischer et al. | |
| 6,655,960 B2 | 12/2003 | Fischer | |
| 6,672,305 B2 | 1/2004 | Parker | |
| 6,716,029 B2 | 4/2004 | Fischer et al. | |
| D495,799 S | 9/2004 | Hirsch et al. | |
| D497,426 S | 10/2004 | Hirsch et al. | |
| 6,908,308 B2 | 6/2005 | Hirsch et al. | |
| 6,974,321 B2 | 12/2005 | Hirsch et al. | |
| 7,287,981 B2 | 10/2007 | Hirsch | |
| 7,293,990 B2 | 11/2007 | Hirsch et al. | |
| D565,186 S | 3/2008 | Huffman | |
| 7,611,354 B2 | 11/2009 | Hirsch et al. | |
| D615,203 S | 5/2010 | Hirsch et al. | |
| 7,748,981 B2 | 7/2010 | Hirsch et al. | |
| 8,029,280 B2 | 10/2011 | Black et al. | |
| 8,057,227 B2 | 11/2011 | Hirsch et al. | |
| 8,057,228 B2 | 11/2011 | Hirsch et al. | |
| 8,075,310 B2 | 12/2011 | Hirsch et al. | |
| D663,831 S | 7/2012 | Sidhu | |
| 8,241,035 B2 | 8/2012 | Jones et al. | |
| D666,726 S | 9/2012 | Davis et al. | |
| 8,297,973 B2 | 10/2012 | Hirsch et al. | |
| D686,327 S | 7/2013 | Marumori | |
| 8,529,256 B2 | 9/2013 | Hirsch et al. | |
| 8,535,056 B2 | 9/2013 | Dragan et al. | |
| D696,779 S | 12/2013 | Hirsch et al. | |
| D706,937 S | 6/2014 | Suga | |
| 8,745,802 B2 | 6/2014 | Steur | |
| 8,911,232 B2 | 12/2014 | Nguyen | |
| D728,108 S | 4/2015 | Coreil | |
| D734,851 S | 7/2015 | Nguyen | |
| 9,084,656 B2 | 7/2015 | Hirsch | |
| 9,089,389 B2 | 7/2015 | Hirsch et al. | |
| D735,858 S | 8/2015 | Hirsch et al. | |
| D737,964 S | 9/2015 | Jessop et al. | |
| D749,716 S | 2/2016 | Holmgren | |
| 9,358,086 B2 | 6/2016 | Hirsch | |
| 9,526,597 B2 | 12/2016 | Steur | |
| 9,532,858 B2 | 1/2017 | Hirsch | |
| D782,047 S | 3/2017 | Ritter | |
| D782,048 S | 3/2017 | Ritter | |
| D787,069 S | 5/2017 | Ritter | |
| D787,070 S | 5/2017 | Ritter | |
| D790,712 S | 6/2017 | Walls | |
| 9,788,924 B2 | 10/2017 | Nguyen | |
| 9,848,959 B2 * | 12/2017 | Lowe .................... A61H 13/00 | |
| D809,660 S | 2/2018 | Nguyen et al. | |
| 9,968,341 B2 | 5/2018 | Ritter | |
| D833,029 S | 11/2018 | Guenst et al. | |
| 10,390,734 B2 | 8/2019 | Johnson et al. | |
| 10,390,916 B1 | 8/2019 | Rassibi | |
| D868,958 S | 12/2019 | Reyes | |
| D876,627 S | 2/2020 | Nguyen et al. | |
| 10,575,976 B2 | 3/2020 | Bardach et al. | |
| D903,096 S | 11/2020 | Hotinsky | |
| 10,869,541 B2 | 12/2020 | Pai et al. | |
| 10,939,979 B2 | 3/2021 | Lombardi | |
| 10,945,593 B1 | 3/2021 | Packouz et al. | |
| D923,796 S | 6/2021 | Mukherji | |
| 11,160,644 B2 | 11/2021 | Glen et al. | |
| 11,191,624 B2 | 12/2021 | Van Dijk | |
| D957,646 S | 7/2022 | Leonhardt | |
| D962,438 S | 8/2022 | Nguyen et al. | |
| D962,439 S | 8/2022 | Nguyen et al. | |
| 11,576,764 B2 * | 2/2023 | Nguyen ............. A61C 17/0208 | |
| 11,589,969 B2 | 2/2023 | Nguyen | |
| 11,589,970 B2 | 2/2023 | Nguyen et al. | |
| 11,737,739 B2 | 8/2023 | Ritter | |
| 11,744,686 B2 | 9/2023 | Nguyen et al. | |
| 11,793,617 B2 | 10/2023 | Cao et al. | |
| 11,826,217 B2 | 11/2023 | Nguyen et al. | |
| 12,011,329 B2 | 6/2024 | Nguyen et al. | |
| D1,033,650 S | 7/2024 | Nguyen et al. | |
| D1,037,436 S | 7/2024 | Nguyen et al. | |
| D1,048,380 S | 10/2024 | Fang | |
| 12,167,948 B2 | 12/2024 | Nguyen et al. | |
| 12,290,418 B2 | 5/2025 | Nguyen et al. | |
| D1,084,352 S | 7/2025 | McCarthy | |
| D1,091,807 S | 9/2025 | Nguyen et al. | |
| D1,097,158 S * | 10/2025 | Ritter ......................... D24/152 | |
| 2001/0008752 A1 | 7/2001 | Hirsch et al. | |
| 2002/0082544 A1 | 6/2002 | Thrash et al. | |
| 2003/0134253 A1 | 7/2003 | Hirsch et al. | |

(56) References Cited

U.S. PATENT DOCUMENTS

| | | | |
|---|---|---|---|
| 2004/0033468 A1 | 2/2004 | Fischer et al. | |
| 2005/0214713 A1* | 9/2005 | O'Neill | A61B 1/24 |
| | | | 433/140 |
| 2006/0063126 A1 | 3/2006 | Aloise et al. | |
| 2006/0063129 A1* | 3/2006 | Hirsch | A61C 1/088 |
| | | | 433/29 |
| 2006/0084031 A1 | 4/2006 | Hirsch et al. | |
| 2008/0166684 A1 | 7/2008 | Kanas | |
| 2008/0318183 A1 | 12/2008 | Suzman | |
| 2009/0117506 A1 | 5/2009 | Igari | |
| 2009/0123886 A1 | 5/2009 | Vaska | |
| 2009/0208898 A1 | 8/2009 | Kaplan | |
| 2009/0274991 A1* | 11/2009 | Black | A61C 17/08 |
| | | | 433/93 |
| 2010/0062397 A1 | 3/2010 | Brewer | |
| 2011/0207076 A1 | 8/2011 | Hirsch et al. | |
| 2011/0311942 A1 | 12/2011 | Black et al. | |
| 2012/0015317 A1 | 1/2012 | Milo | |
| 2012/0015320 A1 | 1/2012 | Koo | |
| 2012/0077144 A1 | 3/2012 | Fougere et al. | |
| 2012/0115102 A1 | 5/2012 | Chen | |
| 2012/0219926 A1* | 8/2012 | Sullivan | A61C 17/0211 |
| | | | 433/80 |
| 2012/0237894 A1 | 9/2012 | Maycher et al. | |
| 2013/0055513 A1 | 3/2013 | Meadows et al. | |
| 2013/0074851 A1* | 3/2013 | Herman | A61C 5/90 |
| | | | 128/861 |
| 2013/0081217 A1 | 4/2013 | Jeong | |
| 2013/0095450 A1 | 4/2013 | Ames | |
| 2013/0252193 A1 | 9/2013 | Bowman et al. | |
| 2014/0004478 A1 | 1/2014 | Hirsch et al. | |
| 2014/0162209 A1 | 6/2014 | Nguyen | |
| 2014/0212837 A1 | 7/2014 | Nguyen | |
| 2014/0212838 A1 | 7/2014 | Nguyen | |
| 2014/0212839 A1 | 7/2014 | Nguyen | |
| 2014/0212840 A1 | 7/2014 | Nguyen | |
| 2014/0212841 A1 | 7/2014 | Nguyen | |
| 2014/0272761 A1 | 9/2014 | Lowe et al. | |
| 2014/0349249 A1 | 11/2014 | Reyes | |
| 2015/0305842 A1 | 10/2015 | Hirsch et al. | |
| 2015/0335409 A1* | 11/2015 | Hirsch | A61C 17/10 |
| | | | 433/93 |
| 2016/0270892 A1 | 9/2016 | Yoo | |
| 2017/0056143 A1 | 3/2017 | Hyun | |
| 2017/0156831 A1 | 6/2017 | Reyes | |
| 2017/0156832 A1* | 6/2017 | Reyes | A61C 17/08 |
| 2017/0156833 A1* | 6/2017 | Reyes | A61C 5/90 |
| 2018/0125349 A1 | 5/2018 | Lutz | |
| 2018/0153637 A1 | 6/2018 | Al-Shawi et al. | |
| 2018/0368957 A1 | 12/2018 | Hyun | |
| 2019/0099236 A1 | 4/2019 | Jin | |
| 2020/0155284 A1 | 5/2020 | Baker | |
| 2020/0178680 A1 | 6/2020 | Van Dijk | |
| 2020/0253369 A1 | 8/2020 | De Gentile et al. | |
| 2020/0352680 A1* | 11/2020 | Nguyen | A61C 5/90 |
| 2020/0383560 A1 | 12/2020 | Day | |
| 2021/0204923 A1 | 7/2021 | Ritter | |
| 2022/0087799 A1* | 3/2022 | Glen | A61K 8/73 |
| 2022/0378563 A1* | 12/2022 | Cao | A61C 17/10 |
| 2023/0338124 A1 | 10/2023 | Nguyen et al. | |
| 2023/0363747 A1 | 11/2023 | Ritter | |
| 2024/0024072 A1 | 1/2024 | Nguyen et al. | |
| 2024/0115366 A1 | 4/2024 | Rosenberg et al. | |
| 2024/0398527 A1 | 12/2024 | Nguyen et al. | |
| 2024/0423768 A1 | 12/2024 | Nguyen et al. | |
| 2025/0262039 A1 | 8/2025 | Reyes | |
| 2025/0275841 A1 | 9/2025 | Nguyen et al. | |
| 2025/0288400 A1* | 9/2025 | Ritter | A61C 17/12 |
| 2025/0289148 A1 | 9/2025 | Van Zuilen | |

FOREIGN PATENT DOCUMENTS

| | | |
|---|---|---|
| CA | 2851861 | 6/2015 |
| CA | 3139689 | 11/2020 |
| CN | 200420094338.X | 12/2005 |
| CN | 102026587 | 4/2011 |
| CN | 102247140 | 11/2011 |
| CN | 104490483 | 4/2015 |
| CN | 105578986 A | 5/2016 |
| CN | 108366851 A | 8/2018 |
| CN | 114302667 A | 4/2022 |
| CN | 202080043728.6 | 12/2025 |
| CO | 43270 | 2/2025 |
| EP | 2903557 | 8/2015 |
| EP | 3184076 | 6/2017 |
| EP | 3965637 | 3/2022 |
| EP | 3965637 B1 | 12/2024 |
| FR | 2992161 | 12/2013 |
| GB | 2 170 106 | 7/1986 |
| JP | 2016523571 | 8/2016 |
| JP | 2016190064 | 11/2016 |
| JP | 2017-518859 | 7/2017 |
| JP | 2018536525 | 12/2018 |
| JP | 2022-533276 | 7/2022 |
| JP | 7617081 B2 | 1/2025 |
| KR | 100654392 | 12/2006 |
| KR | 101082826 | 11/2011 |
| KR | 20220103035 A | 7/2022 |
| MX | 2021013694 A | 4/2022 |
| MX | 422305 | 5/2025 |
| SG | 11202112319 Y | 10/2024 |
| TW | 202108088 | 3/2021 |
| WO | WO 1999/037238 | 7/1999 |
| WO | WO 2000/42939 | 7/2000 |
| WO | WO 00/61031 | 10/2000 |
| WO | WO 2011/014952 | 2/2011 |
| WO | WO 2015/088577 | 6/2015 |
| WO | WO 2018/126150 | 7/2018 |
| WO | WO 2020/231864 | 11/2020 |

OTHER PUBLICATIONS

Canadian Application No. 3,139,689, Examination Report dated Mar. 5, 2025.
U.S. Appl. No. 18/679,097, Office Action dated Mar. 11, 2025.
U.S. Appl. No. 18/823,885, US, Thein Nguyen, Intraoral Device, filed Sep. 4, 2024.
2020274979, AU, Thien Nguyen, Dental Mouthpiece, filed Nov. 9, 2021.
BR1120210224742, BR, Thien Nguyen, Dental Mouthpiece, filed Nov. 9, 2021.
202117051466, IN, Thien Nguyen, Dental Mouthpiece, filed Nov. 10, 2021.
MX/a/2021/013694, MX, Thien Nguyen, Dental Mouthpiece, filed Nov. 9, 2021.
782154, NZ, Thien Nguyen, Dental Mouthpiece, filed Nov. 9, 2021.
U.S. Appl. No. 29/950,233, US, Thien Nguyen, Mouthpiece, filed Jul. 1, 2024.
U.S. Appl. No. 29/950,231, US, Thien Nguyen, Mouthpiece Moth Prop, filed Jul. 1, 2024.
Plaintiff/Counter-Defendant Solmetex, LLC's Responsive Claim Construction Brief (filed in United States District Court, Western District of Michigan, Southern Division Case No. 1:24-cv-00954-RJJ-MV on Nov. 13, 2025).
Defendant Ascentcare Dental Products, Inc.'s Responsive Claim Construction Brief (filed in United States District Court, Western District of Michigan, Southern Division Case No. 1:24-cv-00954-RJJ-MV on Nov. 13, 2025).
Claim Construction Memorandum Opinion and Order (filed in United States District Court, Western District of Michigan, Southern Division Case No. 1:24-cv-00954-RJJ-MV on Jan. 23, 2026).
Inter Partes Review No. IPR2025-01104, Decision Denying Institution of Inter Partes Review, dated Dec. 23, 2025.
Inter Partes Review No. IPR2025-01175, Decision Denying Institution of Inter Partes Review, dated Dec. 23, 2025.
Australian Application No. 2020274979, Examination Report dated Jan. 20, 2025.
Chinese Application No. 202080043728.6, Second Office Action dated May 31, 2025.

(56)  References Cited

OTHER PUBLICATIONS

Inter Partes Review No. IPR2025-01065, Petition for Inter Partes Review of U.S. Pat. No. 11,826,217 filed Jun. 6, 2025.
Inter Partes Review No. IPR2025-01065, Exhibit No. 1003, Expert Declaration of Dr. Brian P. Black dated Jun. 5, 2025.
Inter Partes Review No. IPR2025-01065, Exhibit No. 1008, Solmetex's Complaint for Patent Infringement against Ascentcare (ECF No. 1), filed Sep. 16, 2024.
Inter Partes Review No. IPR2025-01059, Petition for Inter Partes Review of U.S. Pat. No. 11,744,686 filed May 28, 2025.
Inter Partes Review No. IPR2025-01059, Exhibit No. 1003, Expert Declaration of Dr. Brian P. Black dated May 27, 2025.
Inter Partes Review No. IPR2025-01059, Exhibit No. 1009, Solmetex's Complaint for Patent Infringement against Ascentcare (ECF No. 1), filed Sep. 16, 2024.
Inter Partes Review No. IPR2025-01059, Exhibit No. 1011, Solmetex Infringement Contentions filed Feb. 20, 2025.
Inter Partes Review No. IPR2025-01104, Petition for Inter Partes Review of U.S. Pat. No. 12,011,329 dated Jun. 7, 2025.
Inter Partes Review No. IPR2025-01104, Exhibit No. 1003, Expert Declaration of Dr. Brian P. Black dated Jun. 6, 2025.
Inter Partes Review No. IPR2025-01104, Exhibit No. 1009, Solmetex's Complaint for Patent Infringement against Ascentcare (ECF No. 1), filed Sep. 16, 2024.
Inter Partes Review No. IPR2025-01104, Exhibit No. 1011, Solmetex Infringement Contentions filed Feb. 20, 2025.
Inter Partes Review No. IPR2025-01057, Petition for Inter Partes Review of U.S. Pat. No. 11,589,970 dated May 28, 2025.
Inter Partes Review No. IPR2025-01057, Exhibit No. 1003, Expert Declaration of Dr. Brian P. Black dated May 27, 2025.
Inter Partes Review No. IPR2025-01057, Exhibit No. 1009, Solmetex's Complaint for Patent Infringement against Ascentcare (ECF No. 1), filed Sep. 16, 2024.
Inter Partes Review No. IPR2025-01057, Exhibit No. 1011, Solmetex Infringement Contentions filed Feb. 20, 2025.
Inter Partes Review No. IPR2025-01020, Petition for Inter Partes Review of U.S. Pat. No. 11,589,969 dated May 20, 2025.
Inter Partes Review No. IPR2025-01020, Exhibit No. 1003, Expert Declaration of Dr. Brian P. Black dated May 19, 2025.
Inter Partes Review No. IPR2025-01020, Exhibit No. 1009, Solmetex's Complaint for Patent Infringement against Ascentcare (ECF No. 1), filed Sep. 16, 2024.
Inter Partes Review No. IPR2025-01020, Exhibit No. 1011, Solmetex Infringement Contentions filed Feb. 20, 2025.
Inter Partes Review No. IPR2025-01175, Petition for Inter Partes Review of U.S. Pat. No. 12,290,418 dated Jun. 24, 2025.
Inter Partes Review No. IPR2025-01175, Exhibit No. 1003, Expert Declaration of Dr. Brian P. Black dated Jun. 23, 2025.
Inter Partes Review No. IPR2025-01175, Exhibit No. 1011, Solmetex Infringement Contentions filed Feb. 20, 2025.
Post-Grant Review No. PGR2025-00058, Petition for Post Grant Review of U.S. Pat. No. 12,167,948 dated Jun. 19, 2025.
Post-Grant Review No. PGR2025-00058, Exhibit No. 1003, Expert Declaration of Dr. Brian P. Black dated Jun. 19, 2025.
Post-Grant Review No. PGR2025-00058, Exhibit No. 1008, Solmetex's Complaint for Patent Infringement against Ascentcare (ECF No. 1), filed Feb. 20, 2025.
Post-Grant Review No. PGR2025-00058, Notice of Filing Date Accorded to Petition and Time for Filing Patent Owner Preliminary Response filed Jun. 19, 2025.
"Dryshield Tutorial—Maximize Your Dryshield Experience" posted by Dryshield Isolation System. Youtube. Posting date: Apr. 22, 2015. Retrieval date: Oct. 9, 2025. Retrieved from internet: https://www.youtube.com/watch?v=fEkezLuvsL0 (Year: 2015).
Dxm Ez Bite Block Dental Disposable Mouth Prop, Retrieval date: Oct. 9, 2025. Retrieved from the internet: https://www.amazon.com/dp/BOBCC9BWRF, Reference dated Aug. 29, 2022.
Snawop Dental Bite Blocks, Retrieval date: Oct. 9, 2025 at https://www.amazon.com/dp/B0C4L76KCT/ Reference dated May 8, 2023.

Zirc, "Lingua-Fix Disposable Saliva Ejector 50/Pk. White. Provides a dry work area", Retrieval Date: Oct. 9, 2025. Retrieved from the Internet: https://www.net32.com/ec/linguafix-disposable-saliva-ejector-50-white-provides-d-45720 Reference dated Aug. 15, 2013.
Brazilian Application No. BR112021022474-2, Preliminary Office Action dated Oct. 21, 2025.
U.S. Appl. No. 29/950,231, Office Action dated Oct. 31, 2025.
Inter Partes Review No. IPR2025-01065 Patent Owner's Preliminary Response dated Oct. 15, 2025.
Inter Partes Review No. IPR2025-01065, Exhibits 2019-2024, submitted with Patent Owner's Preliminary Response dated Oct. 15, 2025.
Inter Partes Review No. IPR2025-01065 and Post-Grant Review No. PGR2025-00058 Director Discretionary Decision Refer dated Oct. 17, 2025.
Inter Partes Review Nos. IPR2025-01104 and IPR2025-01175 Director Discretionary Decision Deny dated Oct. 17, 2025.
Inter Partes Review No. IPR2025-01104, Patent Owner's Preliminary Response dated Oct. 15, 2025.
Inter Partes Review No. IPR2025-01104, Exhibits 2029-2040, submitted with Patent Owner's Preliminary Response dated Oct. 15, 2025.
Inter Partes Review Nos. IPR2025-01020, IPR2025-01057, and IPR2025-01059 Director Discretionary Decision Deny dated Oct. 10, 2025.
Inter Partes Review No. IPR2025-01175, Patent Owner's Preliminary Response dated Oct. 22, 2025.
Inter Partes Review No. IPR2025-01175, Exhibits 2031-2042, submitted with Patent Owner's Preliminary Response dated Oct. 22, 2025.
Defendant's Initial Invalidity Contentions (filed in United States District Court, Western District of Michigan, Southern Division Case No. 1:24-cv-00954-RJJ-MV on Aug. 18, 2025).
Defendant's Initial Invalidity Contentions, Exhibits A-J (filed in United States District Court, Western District of Michigan, Southern Division Case No. 1:24-cv-00954-RJJ-MV on Aug. 18, 2025).
Solmetex, LLC's Opening Brief in Support of Claim Construction (filed in United States District Court, Western District of Michigan, Southern Division Case No. 1:24-cv-00954-RJJ-MV on Oct. 10, 2025).
Declaration of Professor Charles Garris, Ph.D., Exhibit L, Regarding Claim Construction, submitted with Solmetex, LLC's Opening Brief in Support of Claim Construction (filed in United States District Court, Western District of Michigan, Southern Division Case No. 1:24-cv-00954-RJJ-MV on Oct. 10, 2025).
Defendant/Counter-Plaintiff Ascentcare Dental Products, Inc's Opening Markman Brief (filed in United States District Court, Western District of Michigan, Southern Division Case No. 1:24-cv-00954-RJJ-MV on Oct. 10, 2025).
Declaration of Nathan P. Sportel in Support of Defendant/Counter-Plaintiff's Opening Markman Brief, with Exhibit O Shen Declaration and Exhibit P Crossman Declaration (filed in United States District Court, Western District of Michigan, Southern Division Case No. 1:24-cv-00954-RJJ-MV on Oct. 10, 2025).
Inter Partes Review No. IPR2025-01065, Petitioner's Response to Patent Owner's Brief on Discretionary Denial dated Sep. 30, 2025.
Inter Partes Review No. IPR2025-01065, Exhibits 1024-1026, submitted with Petitioner's Response to Patent Owner's Brief on Discretionary Denial dated Sep. 30, 2025.
Inter Partes Review No. IPR2025-01059, Patent Owner's Preliminary Response dated Oct. 1, 2025.
Inter Partes Review No. IPR2025-01059, Exhibits 2026-2037, Patent Owner's Preliminary Response dated Oct. 1, 2025.
Inter Partes Review No. IPR2025-01059, Petitioner's Response to Patent Owner's Brief on Discretionary Denial dated Sep. 24, 2025.
Inter Partes Review No. IPR2025-01059, Exhibits 1027-1032, submitted with Petitioner's Response to Patent Owner's Brief on Discretionary Denial dated Sep. 24, 2025.
Inter Partes Review No. IPR2025-01104, Petitioner's Response to Patent Owner's Brief on Discretionary Denial dated Sep. 30, 2025.
Inter Partes Review No. IPR2025-01104, Exhibits 1025-1032, submitted with Petitioner's Response to Patent Owner's Brief on Discretionary Denial dated Sep. 30, 2025.

(56)            References Cited

OTHER PUBLICATIONS

Inter Partes Review No. IPR2025-01057, Patent Owner's Preliminary Response dated Sep. 23, 2025.
Inter Partes Review No. IPR2025-01057, Exhibits 2026-2037, submitted with Patent Owner's Preliminary Response dated Sep. 23, 2025.
Inter Partes Review No. IPR2025-01057, Petitioner's Response to Patent Owner's Brief on Discretionary Denial dated Sep. 23, 2025.
Inter Partes Review No. IPR2025-01057, Exhibits 1026-1032, submitted with Petitioner's Response to Patent Owner's Brief on Discretionary Denial dated Sep. 23, 2025.
Inter Partes Review No. IPR2025-01020, Petitioner's Sur-Reply to Patent Owner's Brief on Discretionary Denial dated Sep. 25, 2025.
Inter Partes Review No. IPR2025-01020, Patent Owner's Reply in Support of Discretionary Denial dated Sep. 24, 2025.
Inter Partes Review No. IPR2025-01020, Petitioner's Response to Patent Owner's Brief on Discretionary Denial dated Sep. 18, 2025.
Inter Partes Review No. IPR2025-01020, Exhibits 1023-1030, submitted with Petitioner's Response to Patent Owner's Brief on Discretionary Denial dated Sep. 18, 2025.
Inter Partes Review No. IPR2025-01020, Patent Owner's Preliminary Response dated Sep. 18, 2025.
Inter Partes Review No. IPR2025-01020, Exhibits 2016-2026, submitted with Patent Owner's Preliminary Response dated Sep. 18, 2025.
Inter Partes Review No. IPR2025-01175, Petitioner's Response to Patent Owner's Brief on Discretionary Denial dated Oct. 6, 2025.
Inter Partes Review No. IPR2025-01175, Exhibits 1024-1032, submitted with Petitioner's Response to Patent Owner's Brief on Discretionary Denial dated Oct. 6, 2025.
Post-Grant Review No. PGR2025-00058, Petitioner's Response to Patent Owner's Brief on Discretionary Denial dated Oct. 6, 2025.
Post-Grant Review No. PGR2025-00058, Exhibits 1024-1026, submitted with Petitioner's Response to Patent Owner's Brief on Discretionary Denial dated Oct. 6, 2025.
Indian Application No. 202117051466, Hearing Notice dated Aug. 28, 2025.
Philippines Application No. 1-2021-552855, Substantive Examination Report dated Sep. 5, 2025.
Inter Partes Review No. IPR2025-01065, Patent Owner's Discretionary Denial Brief filed Sep. 2, 2025.
Inter Partes Review No. IPR2025-01065, Exhibits 2001-2018, submitted with Patent Owner's Discretionary Denial Brief filed Sep. 2, 2025.
Inter Partes Review No. IPR2025-01059, Patent Owner's Discretionary Denial Brief filed Aug. 25, 2025.
Inter Partes Review No. IPR2025-01059, Exhibits 2001-2024, submitted with Patent Owner's Discretionary Denial Brief filed Aug. 25, 2025.
Inter Partes Review No. IPR2025-01104, Patent Owner's Discretionary Denial Brief filed Sep. 2, 2025.
Inter Partes Review No. IPR2025-01104, Exhibits 2001-2005, 2007-2013, and 2015-2028, submitted with Patent Owner's Discretionary Denial Brief filed Sep. 2, 2025.
Inter Partes Review No. IPR2025-01057, Patent Owner's Discretionary Denial Brief filed Aug. 25, 2025.
Inter Partes Review No. IPR2025-01057, Exhibits 2001, 2002 and 2004-2025, submitted with Patent Owner's Discretionary Denial Brief filed Aug. 25, 2025.
Inter Partes Review No. IPR2025-01020, Patent Owner's Discretionary Denial Brief filed Aug. 17, 2025.
Inter Partes Review No. IPR2025-01020, Exhibits 2001-2015, submitted with Patent Owner's Discretionary Denial Brief filed Aug. 17, 2025.
Inter Partes Review No. IPR2025-01175, Patent Owner's Discretionary Denial Brief filed Sep. 8, 2025.
Inter Partes Review No. IPR2025-01175, Exhibits 2001-2005, 2007-2013, and 2015-2030, submitted with Patent Owner's Discretionary Denial Brief filed Sep. 8, 2025.

Post-Grant Review No. PGR2025-00058, Patent Owner's Discretionary Denial Brief filed Sep. 8, 2025.
Post-Grant Review No. PGR2025-00058, Exhibits 2001-2022, submitted with Patent Owner's Discretionary Denial Brief filed Sep. 8, 2025.
Post-Grant Review No. PGR2025-00058, Notice of Filing Date Accorded to Petition and Time for Filing Patent Owner Preliminary Response Jul. 8, 2025.
Dryshield brochure. Dryshield.com. Publish date: May 2019. Retrieval date: Sep. 15, 2021. Retrieved from internet: https://dryshield.com/ds/Brochure_May2019.pdf (Year: 2019).
"Dryshield (single-use) vs. Zryis/Isolite (single-use) mouthpieces" posted by Mark Frias, RDH. Youtube. Posting date: Jan. 18, 2020. Retrieval date: Sep. 15, 2021. Retrieved from internet: https://www.youtube.com/watch?v=uKX9XahOEY (Year: 2020).
"Dryshield Presentation (Learn all about Dryshield)" posted by Dryshield isolation System. Youtube. Posting date: Oct. 27, 2014. Retrieval date: Sep. 15, 2021. Retrieved from internet: https://www.youtube.com/watch?v=fcbpz3ixvis (Year: 2014).
"Dryshield Tutorial—Maximize Your Dryshield Experience" posted by Dryshield Isolation System. Youtube. Posting date: Apr. 15, 2015. Retrieval date: Sep. 15, 2021. Retrieved from internet: https://www.youtube.com/watch?v=L2OSYPS8Rc4 (Year: 2015).
PCT Application No. PCT/US2014/032892, International Preliminary Report on Patentability dated Jun. 14, 2016.
PCT Application No. PCT/US2014/032892, International Search Report and Written Opinion dated Sep. 4, 2014.
PCT Application No. PCT/US2020/032228, International Preliminary Report on Patentability dated Nov. 16, 2021.
PCT Application No. PCT/US2020/032228, International Search Report and Written Opinion dated Aug. 12, 2020.
Australian Application No. 2014202637, AU Examination Report dated Jan. 23, 2015.
Brazilian Application No. BR1120140116377, Preliminary Office Action Jan. 7, 2020.
Canadian Application No. 2,919,142, CA Examination Report dated May 31, 2016.
Chinese Application No. 201480039991.2, First Office Action dated Dec. 29, 2016.
Chinese Application No. 202080043728.6, First Office Action dated Oct. 28, 2024.
Columbian Application No. NC2021/0016591, First Substantive Examination dated Jan. 30, 2024.
European Application No. 14721736.8, Extended European Search Report dated Oct. 20, 2015.
European Application No. 17150671.0, Extended European Search Report dated May 29, 2017.
European Application No. 20804801.7, Extended European Search Report dated Apr. 20, 2023.
European Application No. 20804801.7, Supplementary European Search Report dated May 10, 2023.
Indian Application No. 202117051466, First Examination Report dated Nov. 9, 2023.
Japanese Application No. 2022-514453, Non-Final Notification of Reasons for Refusal dated Jan. 30, 2024.
Japanese Application No. 2022-514453, Final Notification of Reasons for Refusal dated Jun. 25, 2024.
Mexican Application No. MX/a/2021/013694, Official Action dated Oct. 2, 2024.
New Zealand Application No. 782154, Examination Report dated Jan. 5, 2024.
New Zealand Application No. 782154, Examination Report dated Jul. 2, 2024.
New Zealand Application No. 782154, Examination Report dated Oct. 9, 2024.
Singaporean Application No. 11202112319Y, Search Report and Written Opinion dated Dec. 21, 2023.
Singaporean Application No. 11202112319Y, Examination Report dated Jun. 29, 2024.
U.S. Appl. No. 14/100,323, Final Office Action dated Oct. 24, 2014.
U.S. Appl. No. 14/100,323, Office Action dated May 6, 2014.
U.S. Appl. No. 14/228,046, Office Action dated Oct. 6, 2021.
U.S. Appl. No. 14/228,046, Final Office Action dated Nov. 27, 2020.

(56) References Cited

OTHER PUBLICATIONS

U.S. Appl. No. 14/228,046, Office Action dated Jan. 10, 2020.
U.S. Appl. No. 14/228,046, Final Office Action dated Jul. 15, 2019.
U.S. Appl. No. 14/228,046, Office Action dated Oct. 5, 2018.
U.S. Appl. No. 14/228,046, Final Office Action dated Jan. 16, 2018.
U.S. Appl. No. 14/228,046, Office Action dated Jun. 5, 2017.
U.S. Appl. No. 14/228,046, Office Action dated Nov. 7, 2016.
U.S. Appl. No. 14/228,046, Final Office Action dated Jun. 6, 2016.
U.S. Appl. No. 14/228,046, Office Action dated Nov. 6, 2015.
U.S. Appl. No. 14/228,050, Office Action dated Nov. 4, 2016.
U.S. Appl. No. 14/228,050, Final Office Action dated May 20, 2016.
U.S. Appl. No. 14/228,050, Office Action dated Nov. 6, 2015.
U.S. Appl. No. 14/228,054, Final Office Action dated Jan. 3, 2022.
U.S. Appl. No. 14/228,054, Office Action dated Jun. 25, 2021.
U.S. Appl. No. 14/228,054, Final Office Action dated Dec. 22, 2020.
U.S. Appl. No. 14/228,054, Office Action dated Jan. 13, 2020.
U.S. Appl. No. 14/228,054, Final Office Action dated Aug. 8, 2019.
U.S. Appl. No. 14/228,054, Office Action dated Nov. 29, 2018.
U.S. Appl. No. 14/228,054, Final Office Action dated Nov. 2, 2017.
U.S. Appl. No. 14/228,054, Office Action dated Apr. 24, 2017.
U.S. Appl. No. 14/228,054, Office Action dated Dec. 3, 2015.
U.S. Appl. No. 14/228,057, Final Office Action dated Jan. 5, 2023.
U.S. Appl. No. 14/228,057, Office Action dated Sep. 2, 2022.
U.S. Appl. No. 14/228,057, Final Office Action dated Nov. 12, 2021.
U.S. Appl. No. 14/228,057, Office Action dated May 5, 2021.
U.S. Appl. No. 14/228,057, Final Office Action dated May 19, 2020.
U.S. Appl. No. 14/228,057, Office Action dated Oct. 7, 2019.
U.S. Appl. No. 14/228,057, Final Office Action dated Mar. 22, 2019.
U.S. Appl. No. 14/228,057, Office Action dated Sep. 7, 2018.
U.S. Appl. No. 14/228,057, Final Office Action dated Nov. 2, 2017.
U.S. Appl. No. 14/228,057, Office Action dated Apr. 13, 2017.
U.S. Appl. No. 14/228,057; Final Office Action dated Jun. 7, 2016.
U.S. Appl. No. 14/228,057, Office Action dated Nov. 20, 2015.
U.S. Appl. No. 14/228,061, Office Action dated Dec. 8, 2021.
U.S. Appl. No. 14/228,061, Final Office Action dated Apr. 29, 2021.

U.S. Appl. No. 14/228,061, Office Action dated Nov. 27, 2020.
U.S. Appl. No. 14/228,061, Final Office Action dated Jan. 10, 2020.
U.S. Appl. No. 14/228,061, Final Office Action dated Jul. 11, 2019.
U.S. Appl. No. 14/228,061, Office Action dated Oct. 4, 2018.
U.S. Appl. No. 14/228,061, Final Office Action dated Oct. 20, 2017.
U.S. Appl. No. 14/228,061, Office Action dated Apr. 12, 2017.
U.S. Appl. No. 14/228,061, Final Office Action dated Jun. 30, 2016.
U.S. Appl. No. 14/228,061, Office Action dated Dec. 4, 2015.
U.S. Appl. No. 18/217,304, Office Action dated Sep. 29, 2023.
U.S. Appl. No. 18/823,885, Office Action dated Nov. 21, 2024.
U.S. Appl. No. 29/491,367, Final Office Action dated Mar. 4, 2015.
U.S. Appl. No. 29/491,367, Office Action dated Nov. 14, 2014.
U.S. Appl. No. 29/477,887, Final Office Action dated Jun. 1, 2016.
U.S. Appl. No. 29/477,887, Office Action dated Nov. 27, 2015.
U.S. Appl. No. 29/477,887, Final Office Action dated May 1, 2015.
U.S. Appl. No. 29/477,887, Office Action dated Nov. 14, 2014.
U.S. Appl. No. 29/477,888, Office Action dated Mar. 21, 2017.
U.S. Appl. No. 29/477,888, Final Office Action dated Jun. 1, 2016.
U.S. Appl. No. 29/477,888, Office Action dated Dec. 2, 2015.
U.S. Appl. No. 29/477,888, Final Office Action dated May 1, 2015.
U.S. Appl. No. 29/477,888, Office Action dated Nov. 14, 2014.
U.S. Appl. No. 16/870,745, Office Action dated Feb. 17, 2023.
U.S. Appl. No. 16/870,745, Final Office Action dated May 12, 2022.
U.S. Appl. No. 16/870,745, Office Action dated Dec. 3, 2021.
U.S. Appl. No. 18/376,309, Office Action dated Jul. 1, 2024.
U.S. Appl. No. 29/782,645, Office Action dated Oct. 4, 2021.
U.S. Appl. No. 29/782,638, Office Action dated Oct. 4, 2021.
U.S. Appl. No. 29/782,644, Final Office Action dated May 11, 2022.
U.S. Appl. No. 29/782,644, Office Action dated Oct. 4, 2021.
U.S. Appl. No. 29/782,643, Final Office Action dated May 11, 2022.
U.S. Appl. No. 29/782,643, Office Action dated Oct. 4, 2021.
U.S. Appl. No. 29/893,986, Ex Parte Quayle Action dated Aug. 15, 2023.
U.S. Appl. No. 29/950,233, Ex Parte Quayle Action dated Sep. 19, 2024.
U.S. Appl. No. 30/016,401, Office Action dated Apr. 1, 2026.

* cited by examiner

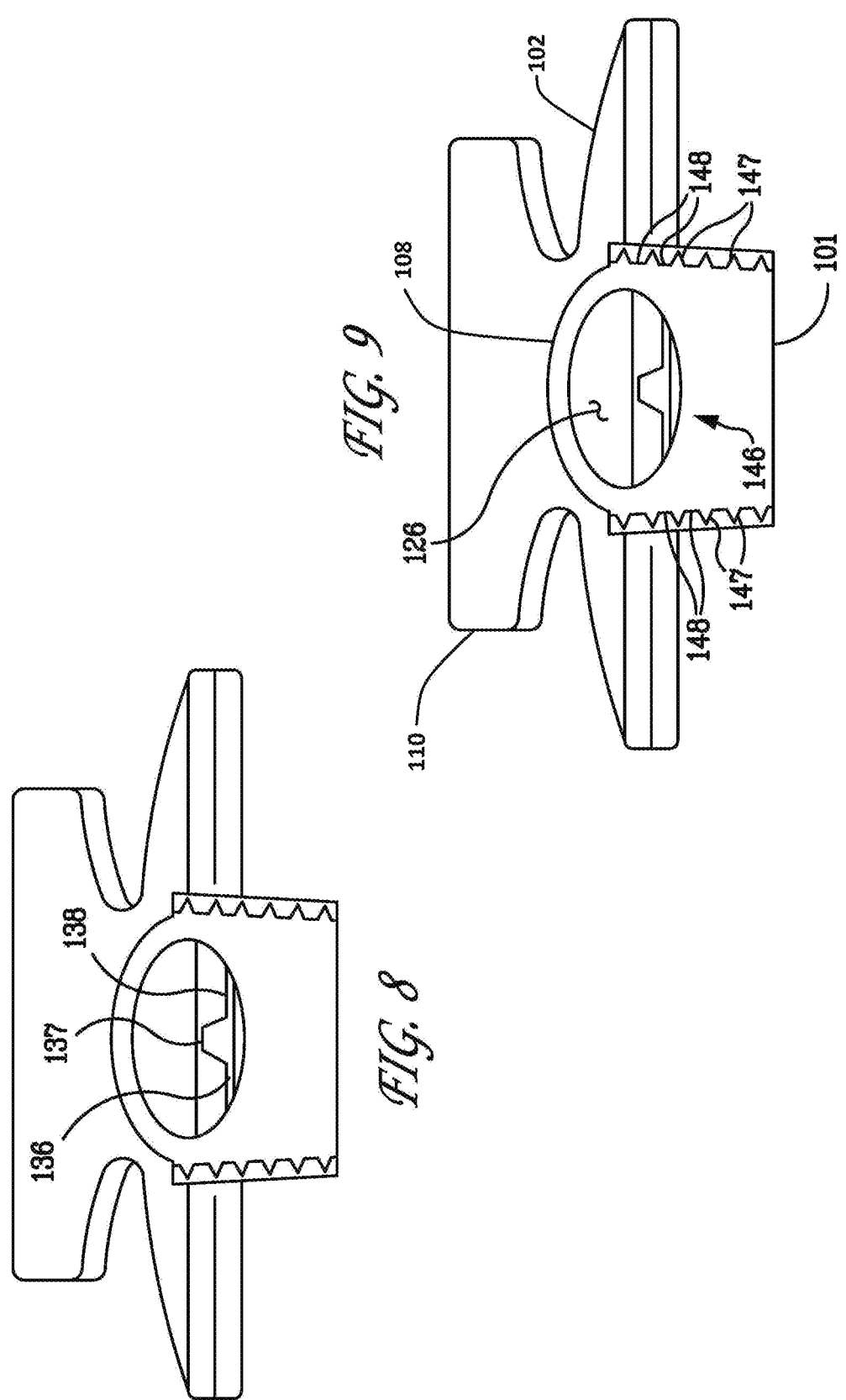

DENTAL MOUTHPIECE

CROSS REFERENCE TO RELATED APPLICATIONS

The present application is a continuation and claims the priority benefit of U.S. application Ser. No. 18/376,309 filed Oct. 3, 2023, now U.S. Pat. No. 12,167,948, which is a continuation and claims the priority benefit of U.S. application Ser. No. 16/870,745 filed May 8, 2020, now U.S. Pat. No. 11,826,217, which claims the priority benefit of U.S. Provisional Application No. 62/846,353 filed May 10, 2019, the disclosures of which are incorporated herein by reference.

BACKGROUND OF THE INVENTION

1. Field of the Invention

The present invention generally relates to the field of dental mouthpieces. More specifically, the present invention relates to intraoral dental suction and isolation mouthpieces.

2. Description of Related Art

Various mouthpieces are currently used by dental health professionals, dental hygienists, and dental assistants in the field of dentistry. In the past, a dental patient has been treated by a traditional two-person team that comprises a dental professional and a dental assistant. Further, dental treatment may be provided by the team using many different types of dental equipment and materials. Such dental equipment and materials may include such items as an intraoral mirror, a bite block, a slow speed suction ejector, a high speed suction ejector, gauzes, cotton rolls, and dry angles. Each item of dental equipment may be used for different purposes, though some may be used in combination for some types of dental services. As such, a dental professional seeking to provide such dental services may need to use multiple items of such dental equipment. An important role of the dental assistant is therefore to assist the dental professional in coordinating the use of these multiple items of different equipment and materials.

There is, therefore, a need in the art for improved systems and methods of providing dental services in a more efficient, comfortable, and safe manner to the dental patient.

SUMMARY OF THE CLAIMED INVENTION

Embodiments of a dental mouthpiece formed in a curve are disclosed. Such a mouthpiece may comprise of a main body portion at a central part of the curve having a first end and a second end, a suction connector portion connected to the main body portion at the first end, and a cheek retractor portion connected to the main body portion at the second end.

In some embodiments, the main body portion, the suction connector portion, and the cheek retractor portion may be molded in one piece, preferably by injection molding. In an exemplary embodiment, the mouthpiece may be made of a material that is flexible, translucent, conductive to injection molding, high heat-resistant, and autoclavable. Such a material may include silicone. Because the mouthpiece may be made of a high heat-resistant and autoclavable material, such a mouthpiece may be reusable.

The main body portion may comprise of an anterior wall inside the curve and a posterior wall outside the curve. The anterior wall and the posterior wall may define an interior space, within which at least one connector connects the anterior wall to the posterior wall. At least one anterior intervening wall extends from the anterior wall partially towards the posterior wall, and at least one posterior intervening wall extends from the posterior wall partially towards the anterior wall. The anterior intervening walls and the posterior intervening walls each has alternating crests and troughs.

BRIEF DESCRIPTION OF THE FIGURES

FIG. 8 is a transverse cross section view of the dental mouthpiece shown in FIG. 1 at the intersection between the suction connector and the main body.

FIG. 9 is a transverse cross section view of the dental mouthpiece shown in FIG. 1 at the intersection between the suction connector and the main body.

DETAILED DESCRIPTION

Embodiments of the present invention may include a mouthpiece that may be attached to a high-suction dental adapter for the purpose of assisting the dental staff during dental procedures through chair-side, hands-free suction, and isolation. Such a mouthpiece may comprise a main body portion, a check retractor portion, a suction connector portion, a stability bar, and a bite block. In some embodiments, any combination of the main body portion, check retractor portion, suction connector portion, a stability bar and bite block (and sub-portions thereof) may be molded in one piece, preferably by injection molding. In an exemplary embodiment, the mouthpiece may be made of a material that is flexible, resilient, at least translucent, and conducive to injection molding. Such a material may include thermoplastic elastomers known in the art.

Figure 1:
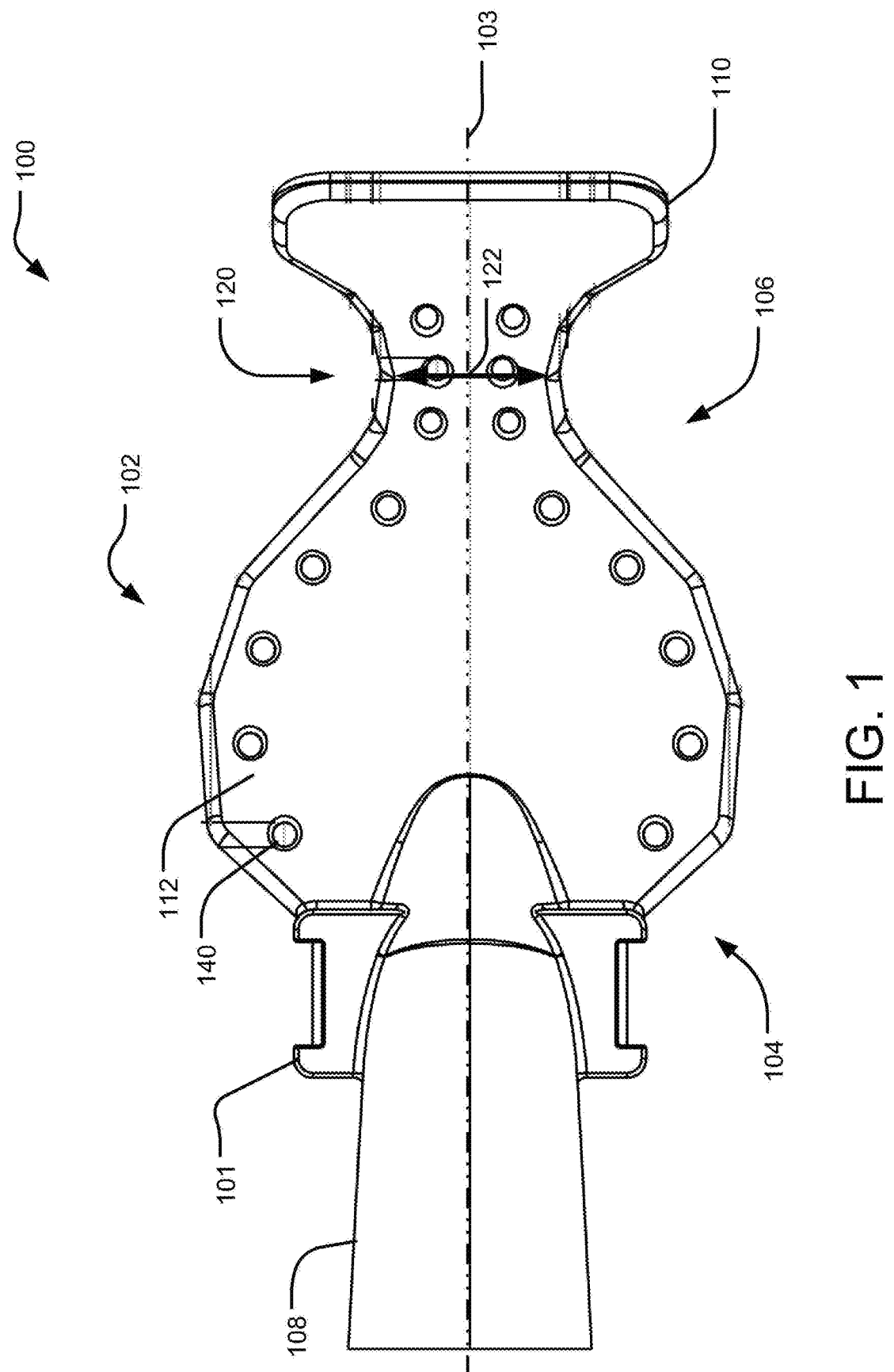
FIG. 1 is a top view of the dental mouthpiece.

FIG. 1 is a top view of the dental mouthpiece. A dental mouthpiece 100 includes a main body portion 102 having a first end 104 and a second end 106 opposite the first end 104. A longitudinal axis 103 may extend from the first end 104 to the second end 106. In the illustrated embodiment, a suction connector portion 108 may be coupled to the first end 104 and a check retractor portion 110 may be coupled to the second end 106, though in other examples the mouthpiece 100 may not have a suction connector portion 108 and/or a check retractor portion 110. A bite block 101 may also be integrated to the suction connector portion 108 near the first end 104 of the main body portion 102, though the bite block 101 may be positioned anywhere on the suction connector portion 108.

The main body portion 101 may include a neck 120 extending from the second end 106 to the check retractor portion 110. The neck 120 may have a width 122 that is less than a width of the main body portion 102, a width of the check retractor portion 110, and/or a width of the suction connector portion 108, though the width 122 may be greater than the width of the main body portion 102, the check retractor portion 110, and/or the suction connector portion 108 in other examples.

In the illustrated embodiment, the suction connector portion 108, the check retractor portion 110, the bite block 101, and the main body portion 102 are constructed as one piece, though in other examples each of the suction connector portion 108, the cheek retractor portion 110, the bite block 101, and/or the main body 102 may be separate pieces. For example, in some embodiments, the main body portion 102, the cheek retractor portion 110, and the suction connector portion 108 (and sub-portions thereof) may be molded as one-piece, preferably by injection molding and the bite block 101 may be a separate piece attachable to the suction connector portion 108. In an exemplary embodiment, the mouthpiece 100 may be made of a material that is flexible, resilient, translucent, and conducive to injection molding. Such a material may include thermoplastic elastomer.

Figure 2:
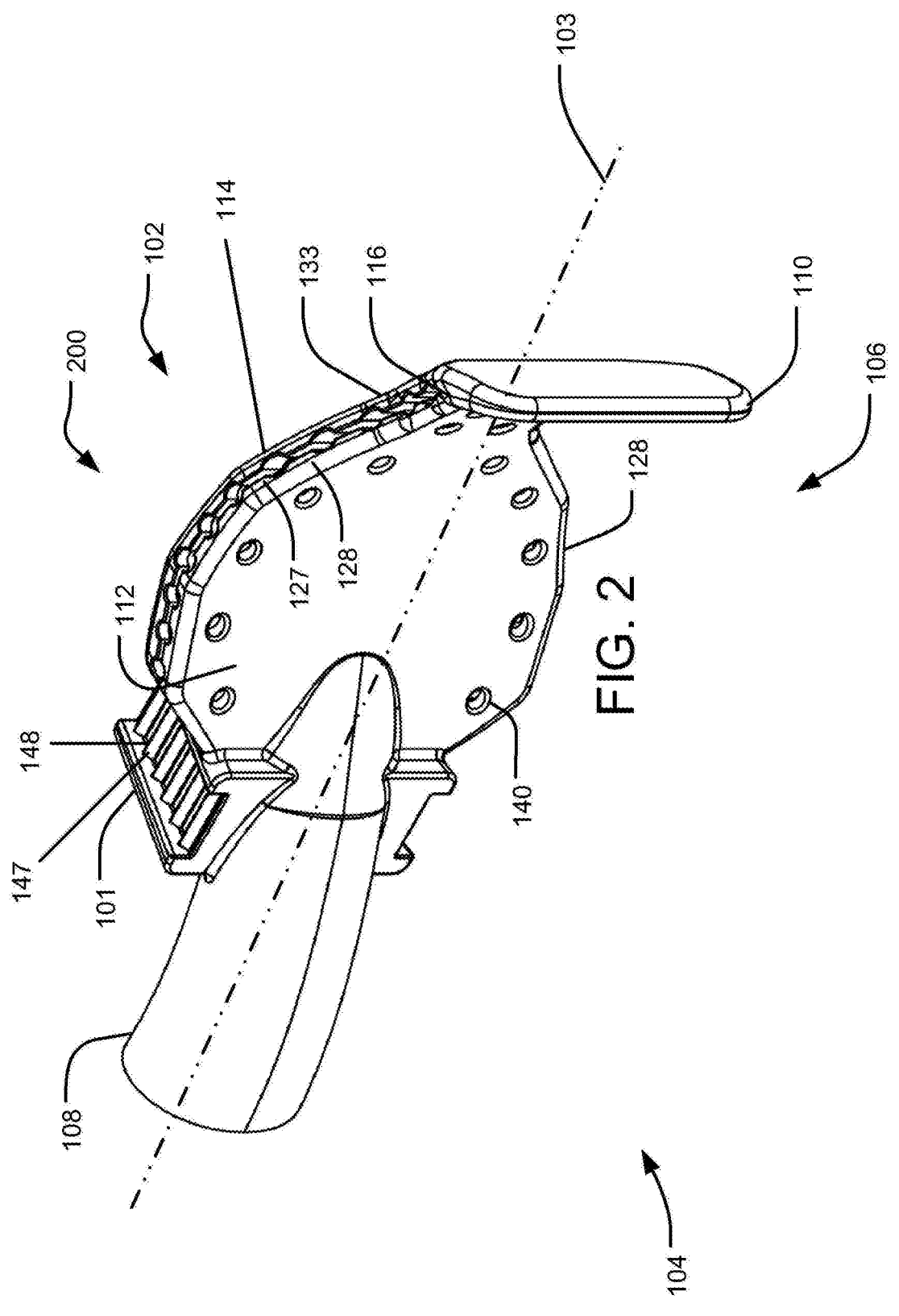
FIG. 2 is an isometric view of a dental mouthpiece shown in FIG. 1.

FIG. 2 is an isometric view 200 of a dental mouthpiece. As illustrated in FIG. 2, the main body portion 102 may be shaped in a curve. Because the mouthpiece 100 is made of a flexible and resilient material (e.g., thermoplastic elastomer), the mouthpiece 100 may be bent when placed in a patient's mouth to conform to the shape of the mouth. When properly positioned, the suction connector portion 108 may protrude from one side of the patient's mouth, while the main body portion 102 lies against the back of the patient's mouth, and the cheek retractor portion 110 presses against the patient's cheek on the opposite side of the patient's mouth.

The check retractor portion 110 may be configured to press against and retract a patient's check away from the patient's teeth on an opposite side of the patient's mouth than the side from which the connection portion 108 extends. The flexibility of the material used to form the mouthpiece 100 allows for some bending when placed in the patient's mouth, but the resilience of the material further allows the mouthpiece 100 to apply pressure against a part of the patient's mouth when the mouthpiece 100 is released from bending. The material is resilient enough, for example, to allow the check retractor portion 110 to press against the inside of the patient's check with such pressure being sufficient to move the check away from the patient's teeth. The cheek retractor portion 110 is illustrated as a hammerhead distal region, which may be attached to the main body portion 102. The cheek retractor portion 110 may be solid in some examples, though may be hollow in other examples.

The main body portion 102 may comprise an anterior wall 112 on an inner part of the curve and a posterior wall 114 (also seen in FIG. 4) on an outer part of the curve. The anterior wall 112 may face a front of the patient's mouth and the posterior wall 114 may face a back of the patient's mouth. The anterior wall 112 and the posterior wall 114 of the main body portion 102 may be configured in parallel to each other. The anterior wall 112 has a defined shape that may correspond to the defined shape of the posterior wall 114, though the anterior wall 112 may be a different shape than the posterior wall 114 in other examples. The defined shape may be wider at the first end 104 and narrower at the second end 106. In some embodiments, the shape corresponds to a shield shape though the shape may be, for example, a square, a straight line arrow, a rectangle, a star, an oval, a circle, or a shape that generally conforms to the intraoral shape of the patient's mouth. Differently-sized mouthpieces may be provided for differently-sized mouths of adults and children. Part of the shape at the first end 104 may be formed with thicker walls than the rest of the main body portion 102. Such thickening may provide additional stability at the first end 104. When positioned within the mouth of a patient, the anterior wall 112 and the posterior wall 114 are capable of blocking an airway of the patient, while the bite block 101 is positioned between the patient's teeth, the suction connector portion 108 extends from one side of the patient's mouth, and the cheek retractor portion 110 presses against the cheek on the opposite side of the patient's mouth.

The main body portion 102 may also include openings 140 located on the anterior wall 112 and/or the posterior wall 114. Such openings 140 (e.g., perforations, slit, aperture, etc.) allow for suction of air, fluids, and small debris from the patient's mouth through the openings 140 and into the interior space 126, and into the suction connector portion 108 towards a suction source. The openings 140 may be positioned on a perimeter of the shape of the anterior wall 112 and/or the posterior wall 114. In the same example, the openings 140 may be positioned on either side of the neck 120 on the anterior wall 112 and/or the posterior wall 114. In another example, the openings 140 are apertures. In the same example, the apertures are each the same size, though in other examples some or all of the apertures may be different sizes.

Figure 3:
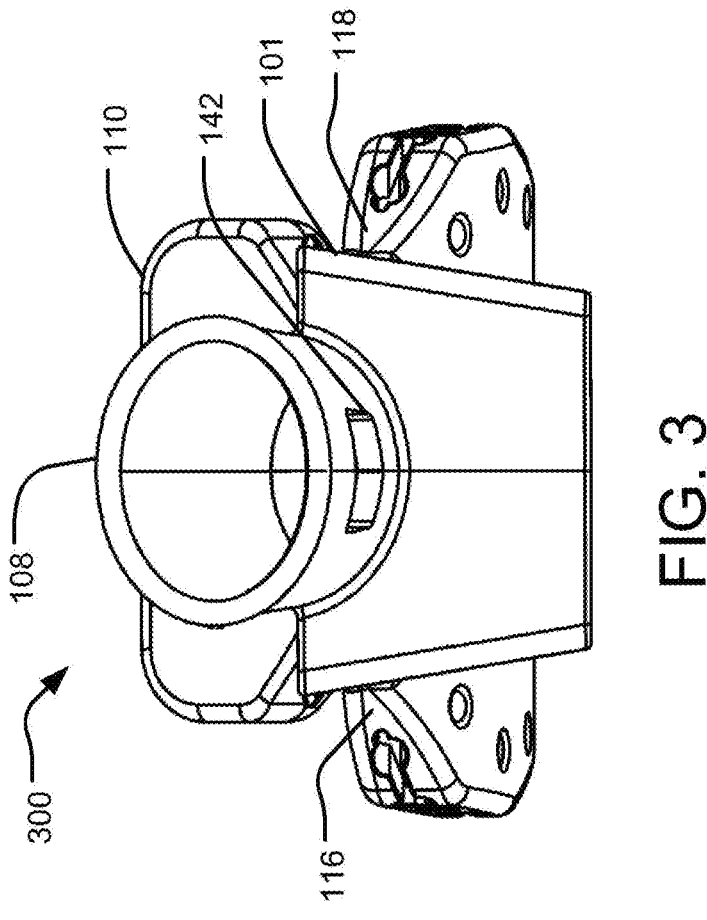
FIG. 3 is a rear view of the dental mouthpiece shown in FIG. 1.

FIG. 3 is a rear view 300 of the dental mouthpiece. As visible in FIG. 3, the suction connector portion 108 may be oval-shaped and also attached to the main body portion 102. The suction connector portion 108 may be formed with thicker walls than the main body portion 102 and configured to attach to a high-suction vacuum adapter and to assist in transferring water, saliva, and debris from the interior space 126 to the external adapter for removal. The suction connector portion 108 may also include an internal stop to assist in sliding the mouthpiece onto the adapter to a desired depth.

The superior wall 116 in FIG. 3 may be used herein to refer to the side that rests against a roof of a patient's mouth when placed therein, and the inferior wall 118 may be used to refer to the side that rests against the floor of the patient's mouth. The superior wall 116 and inferior wall 118 may be formed identically, which may allow for the mouthpiece to change orientation such that the superior wall 116 may appear as the inferior wall 118 and vice versa, in the new orientation. When in use, the superior wall 116 and the inferior wall 118 of the main body portion 101 may serve to protect and separate the top of the mouth and the bottom of the mouth/tongue. In addition, the main body portion 101 may also serve to protect the back of the mouth (e.g., throat and airway) from falling debris.

Figure 4:
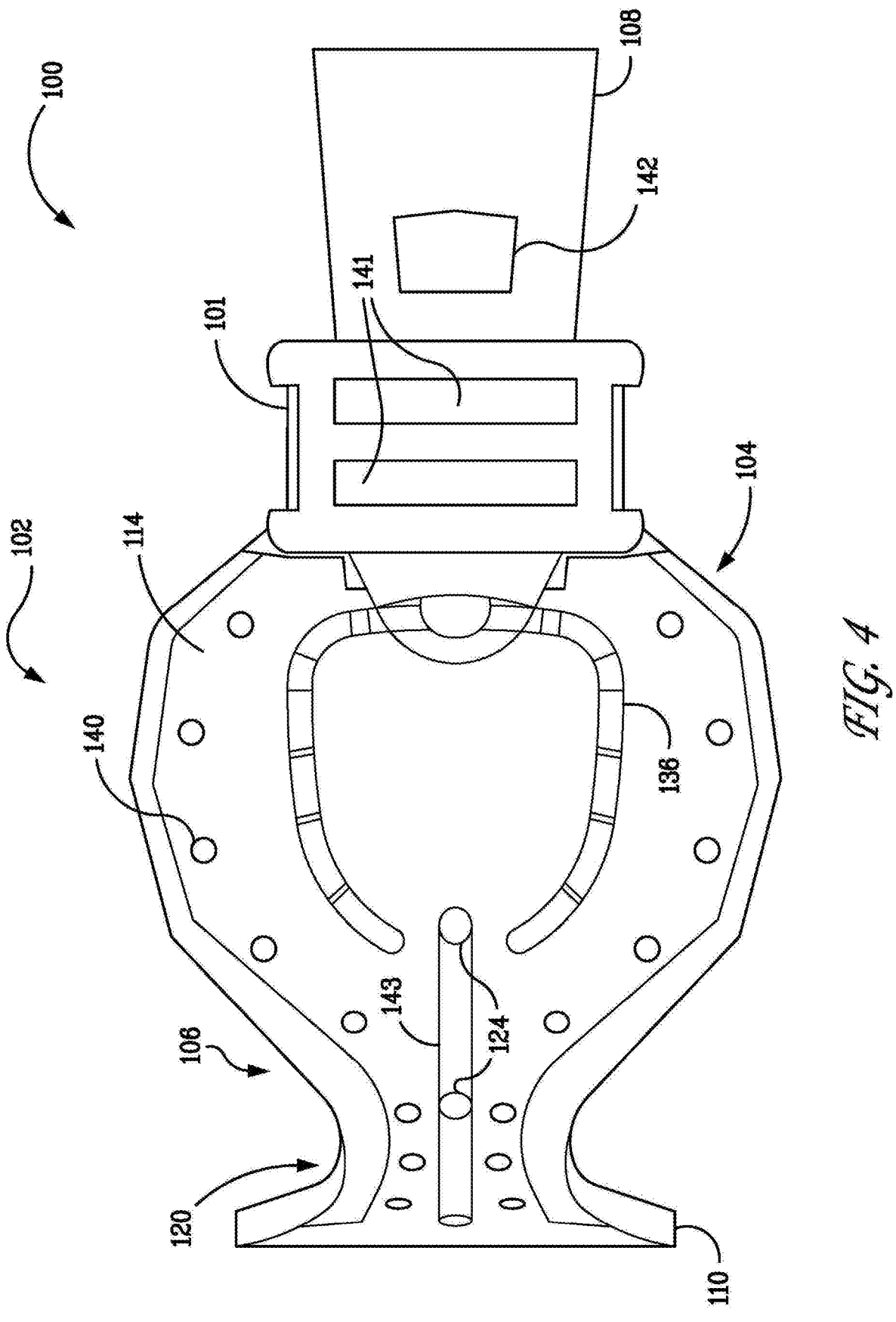
FIG. 4 is a bottom view of the dental mouthpiece shown in FIG. 1.

FIG. 4 is a bottom view of the dental mouthpiece shown in FIG. 1. The anterior wall 112 and the posterior wall 114 may be connected to each other at by at least one connector 124. In some embodiments, the suction connector portion 108 may have a cutout 142 (e.g., which may be shaped as a logo, a rectangular notch, a square notch, or a circular notch, or any shaped notch) providing extra interlocking with a corresponding protrusion (e.g., which may also be shaped as a logo, a rectangular protrusion, a square protrusion, or a circular protrusion, or any shaped protrusion) on an external high-suction vacuum adapter.

The bite block 101 may be reinforced by bite block openings 141 to create cavities in the bite block to result in a more stable bite block. In an embodiment, the bite block openings 141 may be two parallel rectangular openings that open at the bottom of the bite block. The bite block openings 141 may extend up to the suction connector portion 108 but not extending past the thickness of the suction connector portion 108.

Figure 5:
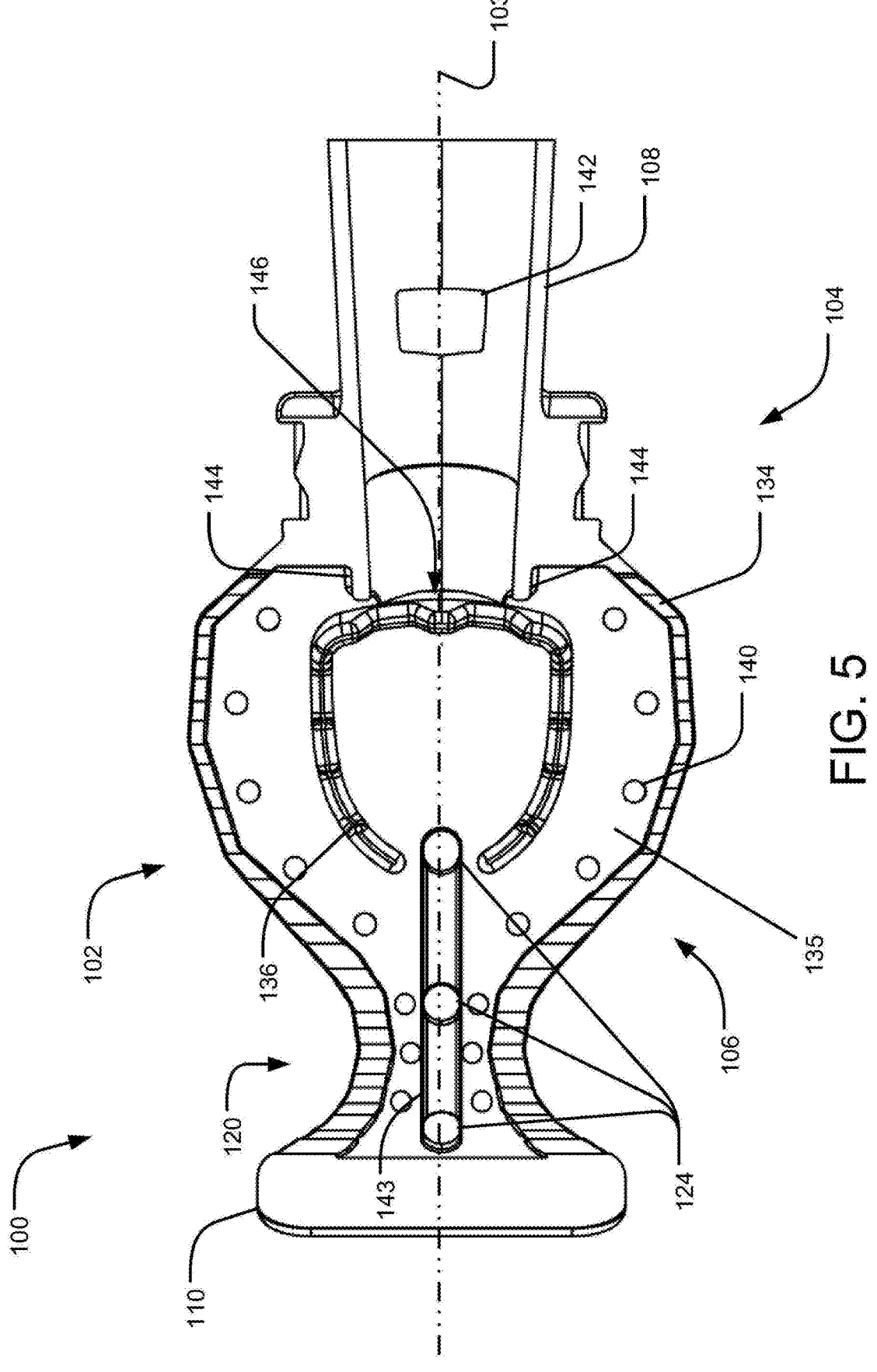
FIG. 5 is a coronal top cross section view of the dental mouthpiece shown in FIG. 1.

FIG. 5 is a coronal top cross section view of the dental mouthpiece shown in FIG. 1. The main body portion 102 may include the bridge structure 136 that protrudes from the interior surface 135 of the posterior wall 114, as shown in FIG. 5 and also visible in FIGS. 7 and 8. In some embodiments, the bridge structure 136 may follow the shape of a logo (e.g., an arrowhead or shield). The bridge structure may have a gap at the tip of the arrowhead shape, creating an open arc instead of a point of an arrow. In some embodiments, the bridge structure 136 may be centrally-located in the main body portion 110 of the mouthpiece 100. In some examples, such bridge structure 136 may protrude from the interior surface 135 in a wave shape with bridge crests 137 and bridge troughs 138. In other embodiments, the bridge structure 136 may protrude in the shape of battlements or trapezoids. The bridge crests 137 provide a plurality of contact points that are generally separate from the anterior wall 112. The bridge crests 137 near the opening 146 of the suction connector portion 108 may have a greater height than the bridge crests 137 further from the opening 146, as visible in FIGS. 7 and 8. The bridge crests 137 near the opening 146 of the suction connection portion 108 may also be longer than the bridge crests 137 further away from the suction connection portion 108 as shown later in FIG. 8. The bridge troughs 138 may be substantially flush or extend above the interior surface 135. The bridge crests 137 contact the anterior wall 112 during suction to keep the anterior wall 112 spaced away from the posterior wall 114 during suction, thereby preventing collapse of the anterior wall 112 or the posterior wall 114 into the interior space 126 so that debris and/or water can be evacuated through the interior space 126. Meanwhile, the bridge troughs 138 provide gaps that allow for suction of air, fluids, and small debris through the bridge structure 136. In other examples, the bridge structure 136 may be smooth, may include sharp crests and sharp troughs, circular crests and circular troughs, square crests and square troughs, or shape or combination of shapes of crests and troughs.

Figure 7:
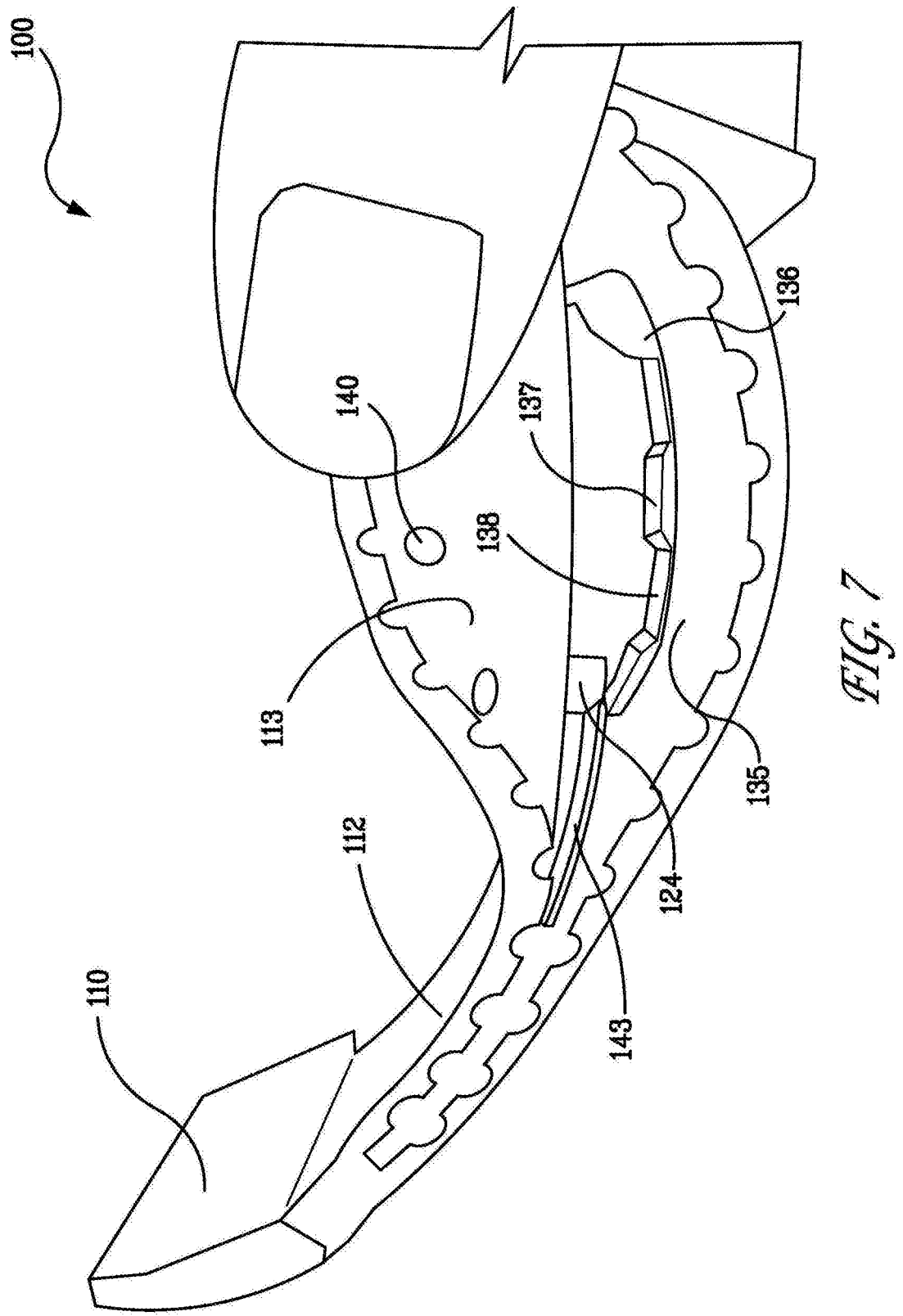
FIG. 7 is a side of the dental mouthpiece shown in FIG. 1 with an anterior wall of the mouthpiece pulled away from a posterior wall of the mouthpiece.

The main body portion 102 may further include a stability bar 143, shown in FIG. 5 and also visible in FIG. 7, that extends from approximately the center of the main body portion 102 toward the check retractor portion 110. Such stability bar 143 may protrude from the interior surface 135 of the posterior wall 114 along the longitudinal axis 103. In an embodiment, the stability bar 143 begins from the open arc of the bridge structure 136 and continue along the longitudinal axis 103 towards the second end 106 past the neck 120 and ends before reaching the check retractor portion 110. The stability bar 143 may protrude from the interior surface 135 of the posterior wall 114 towards the interior surface 113 of the anterior wall 112. The stability bar 143 may be of any height ranging from the height of the interior space 126 or any height less than the interior space 126. In an embodiment, the stability bar 143 may have attached connectors 124 at specific locations that may attach the anterior wall 112 to the posterior wall 114. The connectors 124 on the stability bar 143 may assist with retraction, stability, support and curvature of the mouthpiece 100 during suction. In an exemplary embodiment, there may be multiple connectors 124 aligned with the stability bar 143 the stability bar 143, though the stability bar 143 may not be aligned with the at least one connector 124 in other examples.

Figure 6:
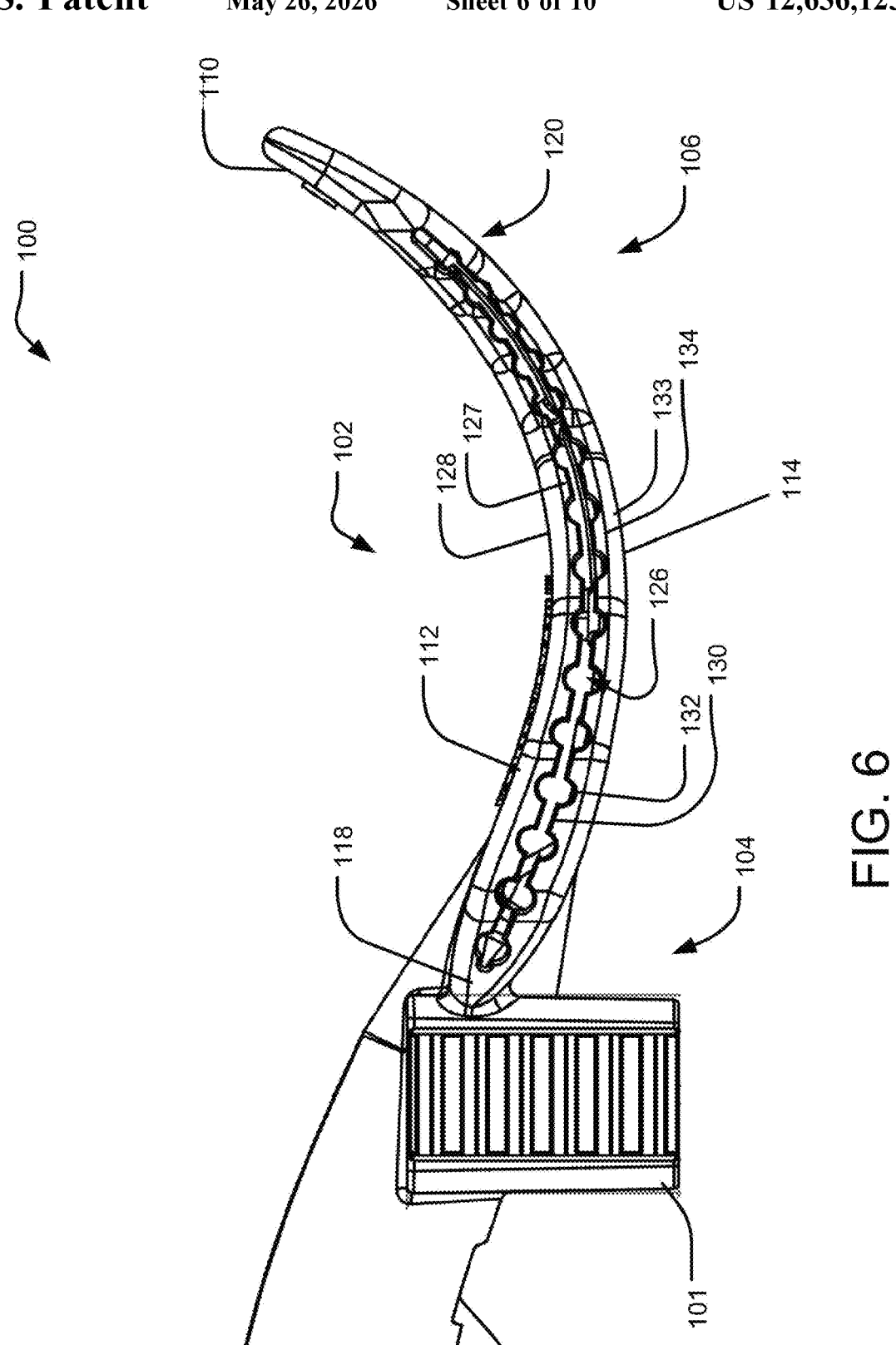
FIG. 6 is a side view of the dental mouthpiece shown in FIG. 1.

FIG. 6 is a side view of the dental mouthpiece shown in FIG. 1. FIG. 6 illustrates the view of the inferior side that rests against the floor of the patient's mouth. The anterior wall 112 and the posterior wall 114 are spaced from each other and define the interior space 126. Other than the at least one connector 124, a stability bar 143, and a bridge structure 136, the interior space 126 is generally open and unobstructed, thereby allowing for suction to flow throughout the interior space 126. The interior space 126 between the anterior wall 112 and the posterior wall 114 generally follows the same defined shape of the anterior wall 112 and the posterior wall 114. In one example, the interior space 126 extends through the neck 120, though in other examples the interior space 126 may not extend through the neck 120. In yet other examples, the interior space 126 extends through the neck 120 and into the cheek retractor portion 120.

At least one anterior intervening wall 127 may extend from at least one edge 128 of the anterior wall 112 partially towards the posterior wall 114 and may have a thickness that extends from the at least one edge 128 to a mid-point between the anterior wall 112 and the posterior wall 114. The span of such anterior intervening wall 127 therefore may not extend the entire distance between the anterior wall 112 and the posterior wall 114. The thickness of such anterior intervening wall 127 may increase from the check retractor portion 110, through the neck 120, and to the first end 104. Such increasing depth may provide for increased rigidity at the first end 104. Such anterior intervening wall 127 may further be ridged in some embodiments, or have a smooth edge in other embodiments. In one example, the anterior intervening wall 127 includes an alternating crest 130 and trough 132. In the illustrated embodiment, the crests 130 are a flat surface and the troughs 132 are a cylindrical cutout surface, though the crests 130 and the troughs 132 may be any shape. In some examples, the crests 130 and the troughs 132 extend the entire depth of the anterior intervening wall 127, though in other examples the crests 130 and/or the troughs 132 may extend partially along the anterior intervening wall 127. The crests 130 and the troughs 132 may provide further retraction, stability, support and curvature to the mouthpiece 100.

The posterior wall 114 may have a corresponding at least one posterior intervening wall 134 that extends from at least one edge 133 of the posterior wall 114 and partially extends towards the anterior wall 112. The posterior intervening wall 134 may likewise exhibit ridges that are the same, a mirror image, or different from the anterior intervening wall 127. In one example, the ridges of the anterior intervening wall 127 may be aligned with the ridges of the posterior intervening wall 134, as shown in FIG. 6. In combination, the anterior intervening wall 127 and the posterior intervening wall 134 and their respective aligned ridges may form an open mesh between the anterior wall 112 and the posterior wall 114. Such open mesh may follow the edges 128, 133 of each of the anterior wall 112 and the posterior wall 114 from the first end 104 to the second end 106. The open mesh between the anterior intervening wall 127 and the posterior intervening wall 134 allows for suction of air, fluids, and small debris from patient's mouth, through the mesh into the interior space 126 and into the suction connector portion 108 towards a suction source.

The anterior intervening wall 127 may join with the posterior intervening wall 134 at the superior wall 116 and the inferior wall 118 at near the suction connector portion 108 of the main body at the first end 104. The anterior intervening wall 127 may also join with the posterior intervening wall 134 at the superior wall 116 and the inferior wall 118 near the check retractor portion 110 at the second end 106. In some embodiments, the anterior intervening wall 127 may join with the posterior intervening wall 134 at the check retractor portion 110.

FIG. 7 is a side of the dental mouthpiece shown in FIG. 1 with an anterior wall of the mouthpiece pulled away from a posterior wall of the mouthpiece. The at least one connector 124 may span the distance between the anterior wall 112 and the posterior wall 114 within the interior space 126. In other words, the connector 124 may be attached to an interior surface 135 of the posterior wall 114 and to an interior surface 113 of the anterior wall 112. The at least one connector 124 may provide structural rigidity to the mouthpiece 100 and may be a pillar, column, wall, or the like. In the illustrated example, the at least one connector 124 includes three connectors, each in the shape of a pillar and linearly spaced from each other.

FIG. 8 is a transverse cross section view of the dental mouthpiece shown in FIG. 1. The bridge crests 137 near the opening 146 of the suction connector portion 108 may have a greater height than the bridge crests 137 further from the opening 146. The bridge crests 137 near the opening 146 of the suction connection portion 108 may also be longer than the bridge crests 137 further away from the suction connection portion 108.

FIG. 9 is a transverse cross section view of the dental mouthpiece in FIG. 1. FIG. 9 illustrates where the suction connector attaches to the main body. As visible in FIG. 9, the suction connector portion 108 may be oval-shaped and also attached to the main body portion 102 in a seamless transition until the main body reaches the bridge structure 136, where the bridge crests 137 and the bridge troughs 138 may partially block the opening of the main body portion 102 near the suction connector portion 108. The bite block 101 is attached on the outside of the suction connector portion 108 such a manner that the bite block does not interrupt the opening of the suction connector portion 108.

The suction connector portion 108 may include an opening 146 (also shown in FIG. 5), that opens into an interior space 126 of the main body portion 102 to allow for fluid communication between the interior space 126 and the suction connector portion 108. At least one suction connector portion wall 144 may extend from the anterior wall 112 to the posterior wall 114 near the opening 146 of the suction connector portion 108 to prevent collapse of the anterior wall 112 and the posterior wall 114 during suctioning. The at least one suction connector portion wall 144 includes a pair of walls positioned on either side of the opening 146 of the suction connector portion 108.

The bite block 101 may include bite block crests 147 and bite block troughs 148 on either sides of the bite block to create greater traction and support for the bite block. In an embodiment, the bite block crests 147 and bite block troughs 148 may create jagged shape or wave shape on either sides of the bite block, although the bite block crests 147 and bite block troughs 148 may be in any shape.

Figure 10:
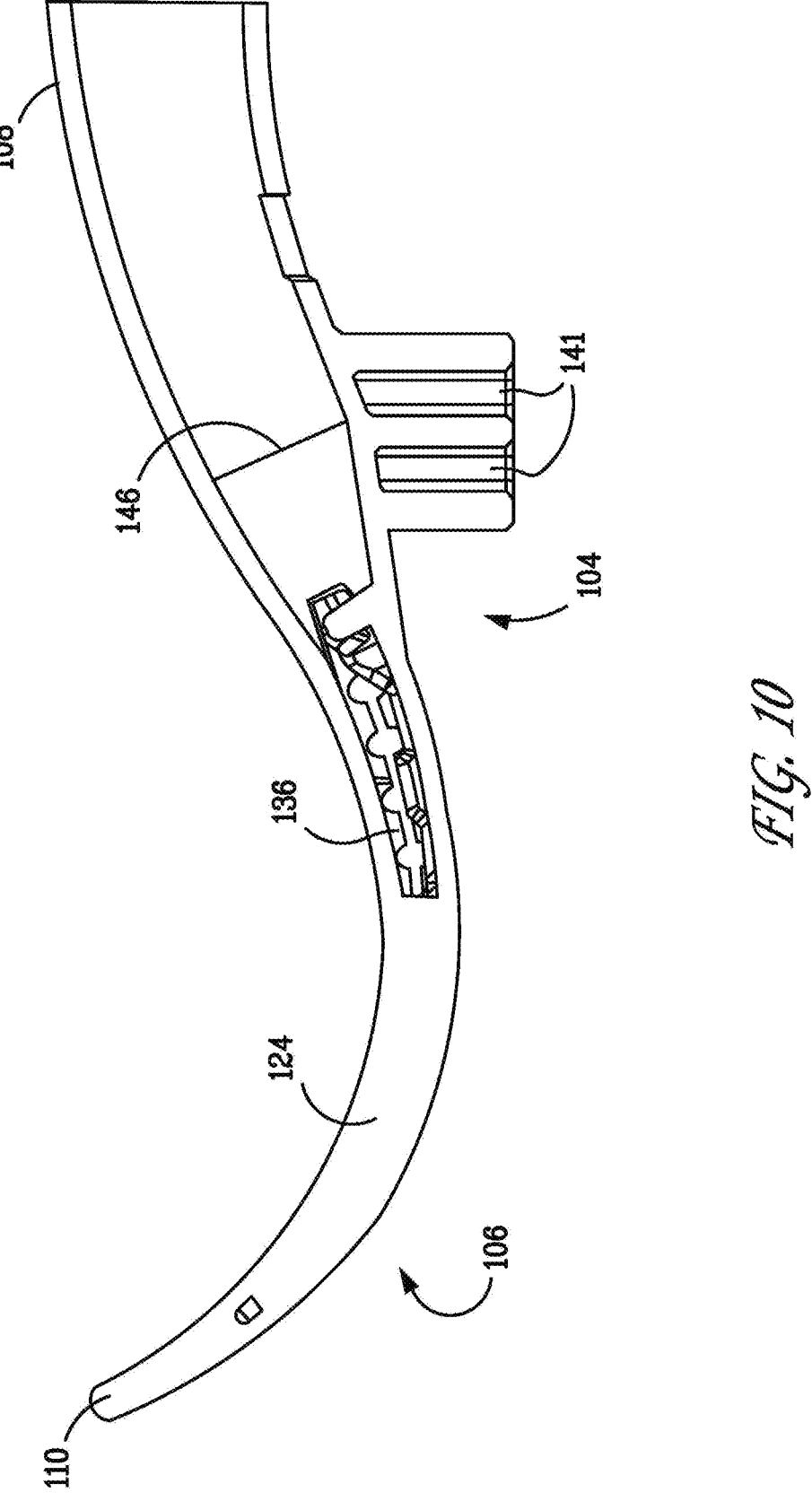
FIG. 10 is a longitudinal cross section view of an embodiment of the dental mouthpiece shown in FIG. 1 with a wall connector.

FIG. 10 is a cross section view of an embodiment of the dental mouthpiece shown in FIG. 1 with a wall connector. In this embodiment, the connector 124 connects the anterior wall 112 with the posterior wall 114 at the longitudinal axis 103 as a solid wall. The connector 124 extends from the neck 120 at the second end 106 some distance away from the check retractor portion 110 towards the first end 104 along the longitudinal axis 103 and stops near the opening of the bridge structure 136 around the mid-point of the main body portion 102. In other embodiment, the connector 124 may extend along the longitudinal axis 103 and stop anywhere within the interior space 126 of the main body portion.

Figure 11:
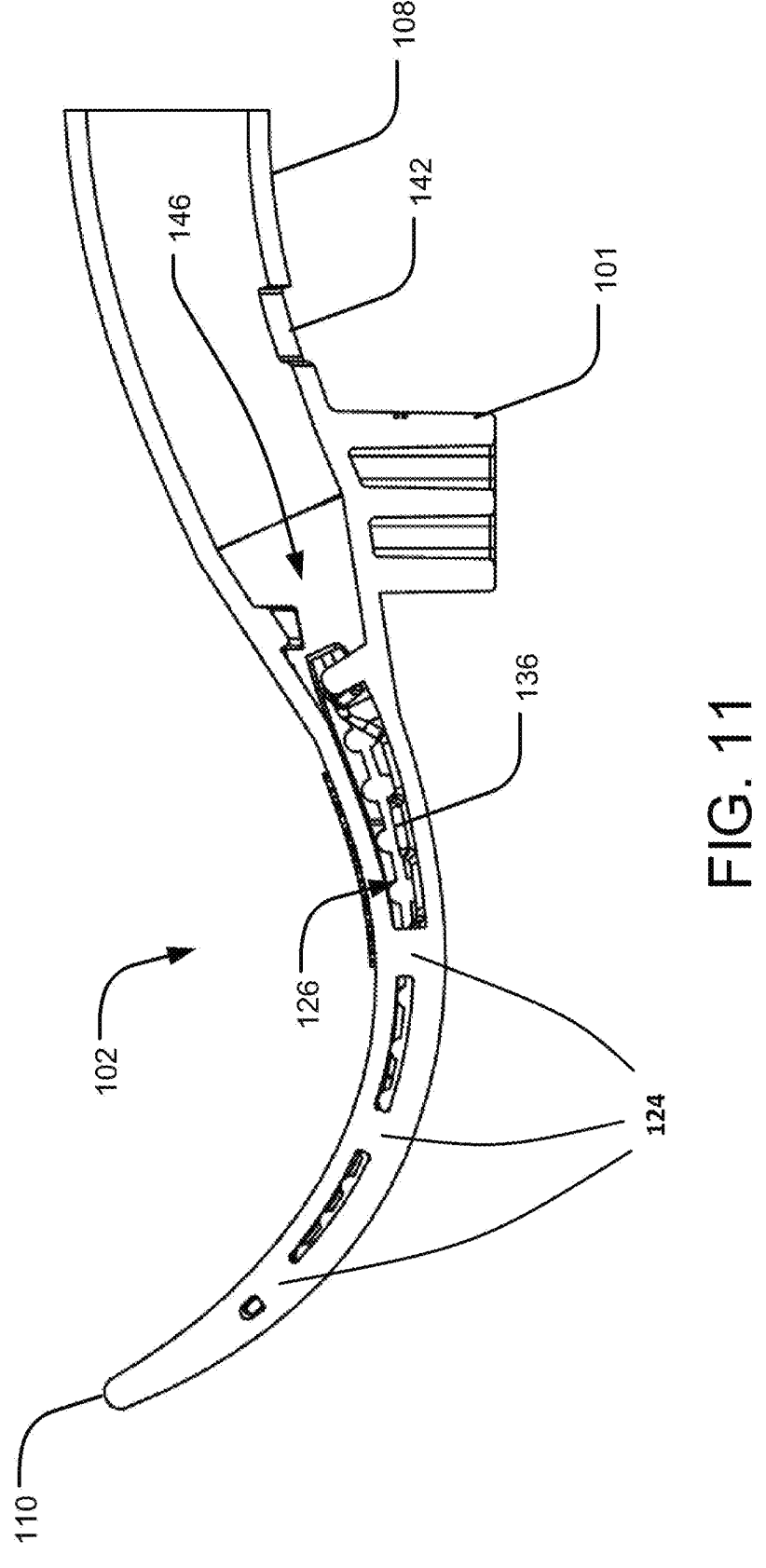
FIG. 11 is a longitudinal cross section view of an embodiment of the dental mouthpiece shown in FIG. 1 with column connectors.

FIG. 11 is a longitudinal cross section view of an embodiment of the dental mouthpiece shown in FIG. 1 with column connectors. In this embodiment, the connector 124 connects the anterior wall 112 with the posterior wall 114 at the longitudinal axis 103 as three evenly spaced cylindrical pillars in line with the stability bar 143. A first connector is positioned in the main body portion 102, a second connector is positioned near the neck 120, and a third connector is spaced near the cheek retractor portion 110. The linear spacing of the three connectors may provide additional rigidity to the neck 120, while maintaining a narrow width 122 of the neck 120. In other examples, such connectors 124 may be located in the area where a positioned mouthpiece 100 begins to wrap from one side of the mouth, to the back of the mouth, then to the other side of the mouth, thereby assisting in shaping the mouthpiece 100 to the general intraoral shape of a patient's mouth. In other examples, the at least one connector 124 may include one connector, two connectors, or more than two connectors and each connector may be positioned anywhere on the mouthpiece 100. In one example, the at least one connector 124 is a rib that extends from the main body portion 102, through the neck 120, and to the cheek retractor portion 110.

The mouthpiece as described herein may be used with a one-piece, autoclavable, high-suction vacuum adapter. Such a high-suction vacuum body adapter may be made of a single homogenous material. Having a single lever design, such a vacuum adapter may function in the same manner as all the current high-suction vacuum evacuators and saliva ejectors in controlling the removal of water, saliva, and debris from the oral cavity to the outside vacuum source. The single lever may be designed to control the removal of water, saliva, and debris from the at least partially enclosed so main body through a single, large evacuation conduit within the suction connector portion.

While various embodiments have been described above, it should be understood that they have been presented by way of example only, and not limitation. The descriptions are not intended to limit the scope of the invention to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the invention as defined by the appended claims and otherwise appreciated by one of ordinary skill in the art. The scope of the invention should, therefore, be determined not with reference to the above description, but instead should be determined with reference to the appended claims along with their full scope of equivalents.

What is claimed is:

1. A mouthpiece comprising:
   a main body portion including a first end and second end,
      the main body portion comprising:

a first wall that includes two edges between the first end
and the second end, a second wall spaced away from the first wall, the first
wall and the second wall define an interior space
between the first wall and the second wall, and a neck portion that extends from the second end of the
main body portion, a width of the neck portion is less
than a width of the main body portion at the first end;

a suction connector portion extending from the first end of
the main body portion, wherein the suction connector
portion includes an evacuation conduit opening into the
interior space of the main body portion;

a cheek retractor portion connected to the neck portion, a
width of the cheek retractor portion is greater than a
width of the neck portion; and a connector wall extending from cheek retractor portion,
through the neck portion, and into the main body
portion, the connector wall connects the first wall to the
second wall within the interior space of the main body
portion and is aligned along a longitudinal axis of the
main body portion, wherein the first wall is configured at the two edges to
have a ridged configuration with alternating crests and
troughs, the crests extending partially across a distance
between the first wall and the second wall, the ridged
configuration of the two edges of the first wall being
unconnected to the second wall such that the first wall
can be pulled away from the second wall, the alternat-
ing crests and troughs of the ridged configuration allow
for suctioning of fluids from a patient's mouth at the
two edges and into the interior space between the first
and second walls.

2. The mouthpiece of claim 1, further including a plurality
of perforations that open into the interior space, the plurality
of perforations being located in the first wall along the two
edges and in the neck portion.

3. The mouthpiece of claim 1, wherein the alternating
crests and troughs of the ridged configuration includes at
least one flat crest.

4. The mouthpiece of claim 1, wherein the alternating
crests and troughs of the ridged configuration includes at
least one semi-circular trough.

5. The mouthpiece of claim 1, wherein the connector wall
is a solid wall.

6. The mouthpiece of claim 1, wherein the connector wall
extends along only a portion of the interior space of the main
body portion.

7. The mouthpiece of claim 1, further comprising a bridge
structure that includes one or more protrusions protruding
from an interior surface of one of the first wall or the second
wall within the interior space, the connector wall terminat-
ing with the interior space at a location adjacent to the bridge
structure.

8. The mouthpiece of claim 1, wherein the suction con-
nector portion includes an oval-shaped tube structure, the
suction connector portion further comprises a bite block
located on an outside surface of and partially surrounding
the oval-shaped tube structure adjacent to the first end of the
main body portion.

9. The mouthpiece of claim 8, wherein the suction con-
nector portion further comprises a cutout in the outside
surface in a shape corresponding to a shape of a protrusion
of a vacuum adapter, the cutout configured to interlock with
the protrusion of the vacuum adapter, the cutout being
located adjacent to the bite block.

10. The mouthpiece of claim 8, wherein the first wall and
the second wall of the main body portion are connected to
the bite block.

11. The mouthpiece of claim 1, wherein the ridged con-
figuration of the first wall is defined by an intervening wall
extending from the first wall toward the second wall.

12. The mouthpiece of claim 1, wherein the first wall has
a shape defined by the two edges that is different from a
shape of the second wall.

13. The mouthpiece of claim 1, wherein the mouthpiece
is formed of a material that includes silicone and is trans-
lucent.

14. A mouthpiece comprising:

a main body portion including a first end and second end,
the main body portion comprising:

a first wall that includes two edges between the first end
and the second end, a second wall spaced away from the first wall, the first
wall and the second wall define an interior space
between the first wall and the second wall, and a neck portion that extends from the second end of the
main body portion;

a suction connector portion extending from the first end of
the main body portion, wherein the suction connector
portion includes a tube-shaped structure that defines an
evacuation conduit opening into the interior space of
the main body portion, the suction connector portion
further comprising a bite block located on an outside
surface of and partially surrounding the tube-shaped
structure adjacent to the first end of the main body
portion, wherein the first wall and the second wall of
the main body portion are connected to the bite block,
and wherein the suction connector portion further com-
prises a cutout in the outside surface that is configured
to interlock with a protrusion of a vacuum adapter, the
cutout being adjacent to the bite block on the outside
surface; and a cheek retractor portion connected to the neck portion, a
width of the cheek retractor portion is greater than a
width of the neck portion, wherein the first wall is configured at the two edges to
have a ridged configuration with alternating crests and
troughs, the crests extending partially across a distance
between the first wall and the second wall and includ-
ing flat crests, the troughs including curved-shaped
troughs, the ridged configuration of the two edges of
the first wall being unconnected to the second wall such
that the first wall can be pulled away from the second
wall, the alternating crests and troughs of the ridged
configuration allow for suctioning of fluids from a
patient's mouth at the two edges through the troughs
and into the interior space between the first wall and the
second wall.

15. The mouthpiece of claim 14, wherein the curved-
shaped troughs include at least one semi-circular trough.

16. The mouthpiece of claim 14, further including a
plurality of perforations that open into the interior space, the
plurality of perforations being located in the first wall along
the two edges and in the neck portion.

17. The mouthpiece of claim 16, wherein there are at least
five of the plurality of perforations located in the first wall
along the two edges.

18. The mouthpiece of claim 14, further including a
connector wall extending from the cheek retractor portion,
through the neck portion, and into the main body portion, the
connector wall connects the first wall to the second wall within the interior space of the main body portion and is aligned along a longitudinal axis of the main body portion.

19. The mouthpiece of claim 18, wherein the connector wall is a solid wall.

20. The mouthpiece of claim 14, wherein a proximal end of the tube-shaped structure of the suction connector portion merges into the second wall of the main body portion at a location between the first end and the second end of the main body.

21. A mouthpiece comprising:

a main body portion including a longitudinal axis, a first end, and a second end, the main body portion comprising:

a first wall having a defined shape that extends from the first end to the second end, a second wall that opposes the first wall and that includes two edges extending between the first end and the second end, the second wall spaced from the first wall so as to define an interior space therebetween, wherein the two edges have a ridged configuration with a plurality of alternating crests and troughs that are unconnected to the first wall such that the two edges of the second wall can be pulled away from the first wall, and wherein the plurality of troughs of the ridged configuration includes troughs that extend different lengths inward toward the longitudinal axis of the main body portion, and a neck portion that extends from the second end of the main body portion;

a suction connector portion extending from the first end of the main body portion, wherein the suction connector portion includes an evacuation conduit opening into the interior space of the main body portion;

a cheek retractor portion connected to the neck portion, a width of the cheek retractor portion is greater than a width of the neck portion; and a connector wall extending from cheek retractor portion, through the neck portion, and into the main body portion, the connector wall connects the first wall to the second wall within the interior space of the main body portion and is aligned along a longitudinal axis of the main body portion.

22. The mouthpiece of claim 21, wherein a first one of the troughs of the ridged configuration at the first end extends a first length from the edge of the second wall toward the longitudinal axis and a second one of the troughs at the second end extends a second length from the edge of the second wall at the second end toward the longitudinal axis.

23. The mouthpiece of claim 22, wherein the different lengths of the troughs increase from the first end to the second end.

24. The mouthpiece of claim 21, wherein the crests of the ridged configuration include flat crests.

25. The mouthpiece of claim 24, wherein the troughs of the ridged configuration define curved openings between the flat crests.

26. The mouthpiece of claim 25, wherein the curved openings of the troughs include openings of different sizes.

27. The mouthpiece of claim 21, wherein the first wall includes a smooth edge.

28. The mouthpiece of claim 21, wherein a proximal end of the suction connector portion merges into the second wall of the main body portion at a location between the first end and the second end of the main body.

29. The mouthpiece of claim 21, wherein the suction connector portion further comprising a bite block located on an outside surface of and partially surrounding an oval-shaped tube structure of the suction connector portion adjacent to the first end of the main body portion, wherein the first wall and the second wall of the main body portion are connected to the bite block.

30. The mouthpiece of claim 21, wherein the first wall and the second wall in the neck portion includes a plurality of perforations.

*  *  *  *  *